United States Patent
Rice et al.

(10) Patent No.: US 11,573,230 B2
(45) Date of Patent: Feb. 7, 2023

(54) RAPID VERIFICATION OF VIRUS PARTICLE PRODUCTION FOR A PERSONALIZED VACCINE

(71) Applicants: NANTCELL, INC., Culver City, CA (US); NANTBIO, INC., Culver City, CA (US)

(72) Inventors: Adrian E. Rice, Culver City, CA (US); Kayvan Niazi, Culver City, CA (US); Frank R. Jones, Culver City, CA (US)

(73) Assignees: NantCell, Inc., Culver City, CA (US); NantBio, Inc., Culver City, CA (US)

( * ) Notice: Subject to any disclaimer, the term of this patent is extended or adjusted under 35 U.S.C. 154(b) by 0 days.

(21) Appl. No.: 16/964,325

(22) PCT Filed: Jan. 25, 2019

(86) PCT No.: PCT/US2019/015126
§ 371 (c)(1),
(2) Date: Jul. 23, 2020

(87) PCT Pub. No.: WO2019/147921
PCT Pub. Date: Aug. 1, 2019

(65) Prior Publication Data
US 2021/0041438 A1  Feb. 11, 2021

Related U.S. Application Data

(60) Provisional application No. 62/622,758, filed on Jan. 26, 2018.

(51) Int. Cl.
*C12Q 1/70* (2006.01)
*G01N 33/569* (2006.01)
(Continued)

(52) U.S. Cl.
CPC ....... *G01N 33/56983* (2013.01); *A61K 39/00* (2013.01); *C12N 15/86* (2013.01);
(Continued)

(58) Field of Classification Search
None
See application file for complete search history.

(56) References Cited

U.S. PATENT DOCUMENTS 6,248,514 B1 * 6/2001 Hutchins .......... G01N 33/56983
435/5
2007/0172846 A1 * 7/2007 Zhang ...................... C12N 7/00
435/6.16
(Continued)

FOREIGN PATENT DOCUMENTS

| WO | WO 2016/112195 | 7/2016 | |
| WO | WO-2017173321 A1 * | 10/2017 | ..... A61K 39/001154 |
| WO | WO 2018/014008 | 1/2018 | |

OTHER PUBLICATIONS

Everitt et al., "A Capture Enzyme-Linked Immunosorbent Assay for Virus Infectivity Titrations as Exemplified in an Adenovirus System", Journal of Immunoassay, 1993, vol. 14(1-2), pp. 1-19.
(Continued)

*Primary Examiner* — M Franco G Salvoza
(74) *Attorney, Agent, or Firm* — Sheridan Ross P.C.

(57) ABSTRACT

Methods for rapidly confirming production of infectious viral vectors, for use in clinical grade personalized neoantigen vaccines for subjects in need thereof, are provided.

12 Claims, 3 Drawing Sheets

Specification includes a Sequence Listing.

(51) Int. Cl.
*A61K 39/00* (2006.01)
*C12N 15/86* (2006.01)

(52) U.S. Cl.
CPC .............. *C12N 2710/10334* (2013.01); *C12N 2710/10343* (2013.01); *C12N 2710/10351* (2013.01)

(56) References Cited

U.S. PATENT DOCUMENTS

2010/0323902 A1* 12/2010 Fang ................ G01N 33/54373
  506/7
2016/0076053 A1* 3/2016 Jones ............... C07K 14/70503
  424/199.1
2017/0056458 A1* 3/2017 Champion ............. C07K 14/56

OTHER PUBLICATIONS

Gabitzsch et al., "The Generation and Analyses of a Novel Combination of Recombinant Adenovirus Vaccines Targeting Three Tumor Antigens as an Immunotherapeutic", Oncotarget, 2015, vol. 6(31), pp. 31344-31359.
Okada et al., "Scalable Purification of Adeno-associated Virus Serotype 1 (AAV1) and AAV8 Vectors, Using Dual Ion-Exchange Adsorptive Membranes", Human Gene Therapy, 2009, vol. 20(9), pp. 1013-1021.
Petersen, "Strategies Using Bio-Layer Interferometry Biosensor Technology for Vaccine Research and Development", Biosensors, 2017, vol. 7(4), Article 49, 15 pages.
Weaver et al, "Evaluation of Adenoviral Vectors by Flow Cytometry", Methods, 2000, vol. 21(3), pp. 297-312.
International Preliminary Report on Patentability for International (PCT) Patent Application No. PCT/US2019/015126 dated Aug. 6, 2020, 8 pages.
International Search Report and Written Opinion for International (PCT) prepared by the European Patent Office for Patent Application No. PCT/US2019/015126 dated Mar. 18, 2019, 11 pages.

* cited by examiner

Triple Gene Insert: ~3.5 kb

Gene Insert: ~3.6 kb

RAPID VERIFICATION OF VIRUS PARTICLE PRODUCTION FOR A PERSONALIZED VACCINE

CROSS REFERENCE TO RELATED APPLICATIONS

This application is a national stage application under 35 U.S.C. 371 of PCT Application No. PCT/US2019/015126, having an international filing date of Jan. 25, 2019, which designated the United States, which PCT application claims the benefit of U.S. Provisional Patent Application No. 62/622,758, filed Jan. 26, 2018, the entire contents of each of which are incorporated by reference herein.

REFERENCE TO SEQUENCE LISTING

This application contains a Sequence Listing submitted as an electronic text file named "8774ETU-27-PCT_Seq_Listing ST25.txt", having a size in bytes of 1000 bytes, and created on Jan. 25, 2019. The information contained in this electronic file is hereby incorporated by reference in its entirety pursuant to 37 CFR § 1.52(e)(5).

BACKGROUND

Vaccines help the body fight disease by training the immune system to recognize and destroy harmful substances and diseased cells. Viral vector-based vaccines are currently being developed to help fight infectious diseases and cancers; however, significant limitations exist in the manufacture and scalability of efficiently and rapidly producing pure batches of virus vectors. In particular, significant challenges remain in cumbersome assay methods currently used to confirm successful production of infective viral particles. Existing assay methods, including hexon-based detection assays, can be time consuming, inefficient, and expensive in terms of reagent and labor costs. As such, there exists a need for improvements in the manufacture of clinical grade vaccines based on viral vectors, particularly at the stage of verifying productive generation of the viral vectors by cells.

The present invention addresses these limitations by introducing an ion-exchange based membrane method of purifying viral vectors from crude cell lysates. In particular, the present invention provides membrane methods purifying viral vector-based vaccines encoding for a neo-antigen or neo-epitope, which can be administered to a patient.

SUMMARY

In various aspects, the present disclosure provides a method of producing a neo-antigen vector, the method comprising: producing the neo-antigen vector; and determining virus infectivity of the neo-antigen vector in a time period of less than 3 days. In some aspects, the determining virus infectivity of the neo-antigen comprises incubating a virion of the neo-antigen vector with a cell. In some aspects, the cell is a suspension cell.

In some aspects, the suspension cell is an E.C7 cell grown in a serum-free media. In further aspects, the suspension cell is a bone marrow-derived cell, a T-lymphoblast-derived cell, or a T cell lymphoma. In further aspects, the bone marrow-derived cell is a K-562 cell. In still further aspects, the T-lymphoblast cell is a MOLT-4 cell. In still further aspects, the T cell lymphoma is a Jurkat E6-1 cell.

In some aspects, the bone marrow-derived cell, the T-lymphoblast-derived cell, or the T cell lymphoma is transfected with adenovirus 5 pol, pTP, E1a, and E1b. In some aspects, the method further comprises centrifuging the cell. In some aspects, the method further comprises incubating the cell with a monoclonal antibody conjugated to a fluorophore. In further aspects, the monoclonal antibody is an anti-hexon monoclonal antibody.

In some aspects, the method further comprises staining the cell with a live/dead stain. In some aspects, the method further comprises performing flow cytometry and selecting for live, hexon-positive cells. In some aspects, the method further comprises correlating the percentage of live, hexon-positive cells to infectious units (IFUs)/mL.

In other aspects, the determining virus infectivity of the neo-antigen comprises loading an E.C7 cell transfected with and propagating the neo-antigen vector onto an optical biosensor. In some aspects, the optical biosensor comprises a glass surface. In some aspects, the optical biosensor comprises a monoclonal antibody. In further aspects, the monoclonal antibody is an anti-hexon monoclonal antibody. In some aspects, the method further comprises measuring mass accumulation on the glass surface by bio-layer interferometry (BLI).

In some aspects, the determining virus infectivity of the neo-antigen is performed in less than 3 days, less than 2 days, less than 1 day, less than 12 hours, less than 6 hours, less than 3 hours, less than 2 hours, less than 1 hours, less than 30 minutes, less than 25 minutes, less than 20 minutes, less than 15 minutes less than 10 minutes, or less than 5 minutes. In further aspects, the determining virus infectivity of the neo-antigen is performed in 5-30 minutes.

In some aspects, the determining virus infectivity of the neo-antigen is performed after the neo-antigen vector has been propagated in an E.C7 cell for 10 days.

In some aspects, the producing the neo-antigen vector comprises: constructing a polynucleotide insert comprising a neo-antigen obtained from a subject; and cloning the polynucleotide insert. In some aspects, cloning the polynucleotide insert comprises gene synthesis, subcloning a shuttle vector, homologous recombination, polymerase chain reaction, enzyme digestion, and transformation of a cell to produce a vector that comprises the neo-antigen obtained from the subject.

In some aspects, the cell is an E.C7 cell. In some aspects, the method further comprises detecting the presence or absence of Carbapenemase-producing Enterobacteriaceae (CPE). In some aspects, the method further comprises passaging the population of cells to obtain passaged cells. In some aspects, the method further comprises quantifying infectious units (IFU)/mL of the neo-antigen vector. In some aspects, quantifying IFU/mL of the neo-antigen vector comprises a hexon assay.

In some aspects, the method further comprises purifying the neo-antigen vector from a cell lysate of the passaged cells. In further aspects, purifying the neo-antigen vector comprises passing the cell lysate of the passage cells through a membrane system, a column, or any combination thereof. In some aspects, the membrane system is an ion-exchange membrane system. In some aspects, the purifying the neo-antigen vector occurs more than once.

In some aspects, the method further comprises performing a silver stain gel analysis. In some aspects, the method further comprises performing a hexon assay and a replication competent Ad (RCA) assay. In some aspects, the method further comprises administering the neo-antigen vector to the subject.

In some aspects, the neo-antigen vector comprises a replication defective viral vector. In further aspects, the replication defective viral vector is an adenoviral vector. In still further aspects, the adenoviral vector is an Ad5 vector. In some aspects, the replication defective viral vector comprises a deletion in an E1 region, an E2 region, and E3 region, an E4 region, or any combination thereof.

In further aspects, the replication defective viral vector comprises a deletion in an E2b region. In some aspects, the neo-antigen vector comprises a nucleic acid sequence encoding for a neo-antigen. In some aspects, the neo-antigen is identified by sequencing a tissue sample from the subject. In some aspects, the method further comprises sequencing the neo-antigen vector to obtain a sequence-verified neo-antigen vector. In further aspects, the sequencing the neo-antigen vector comprises next generation sequencing (massively parallel sequencing).

In some aspects, the subject has a condition. In further aspects, the condition is a cancer. In some aspects, the neo-antigen vector is produced according to FIG. 1. In some aspects, the neo-antigen vector is administered to the subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A illustrates flow cytometry quantification of hexon protein expression in E.C7 cells infected with Ad-CEA. The x-axis indicates the multiplicity of infection (MOI) and the y-axis indicates the percentage of hexon positive cells.

FIG. 2B rates flow cytometry quantification of hexon protein expression in E.C7 cells infected with Ad-Brachyury. The x-axis indicates the multiplicity of infection (MOI) and the y-axis indicates the percentage of hexon positive cells.

FIG. 2C illustrates an overlay of FIG. 2A and FIG. 2B.

FIG. 3A illustrates the pTP, E1a, and E1b triple gene expression plasmid used to transfect suspension cells.

FIG. 3B illustrates the Pol expression plasmid used to transfect suspension cells.

DETAILED DESCRIPTION

Figure 1:
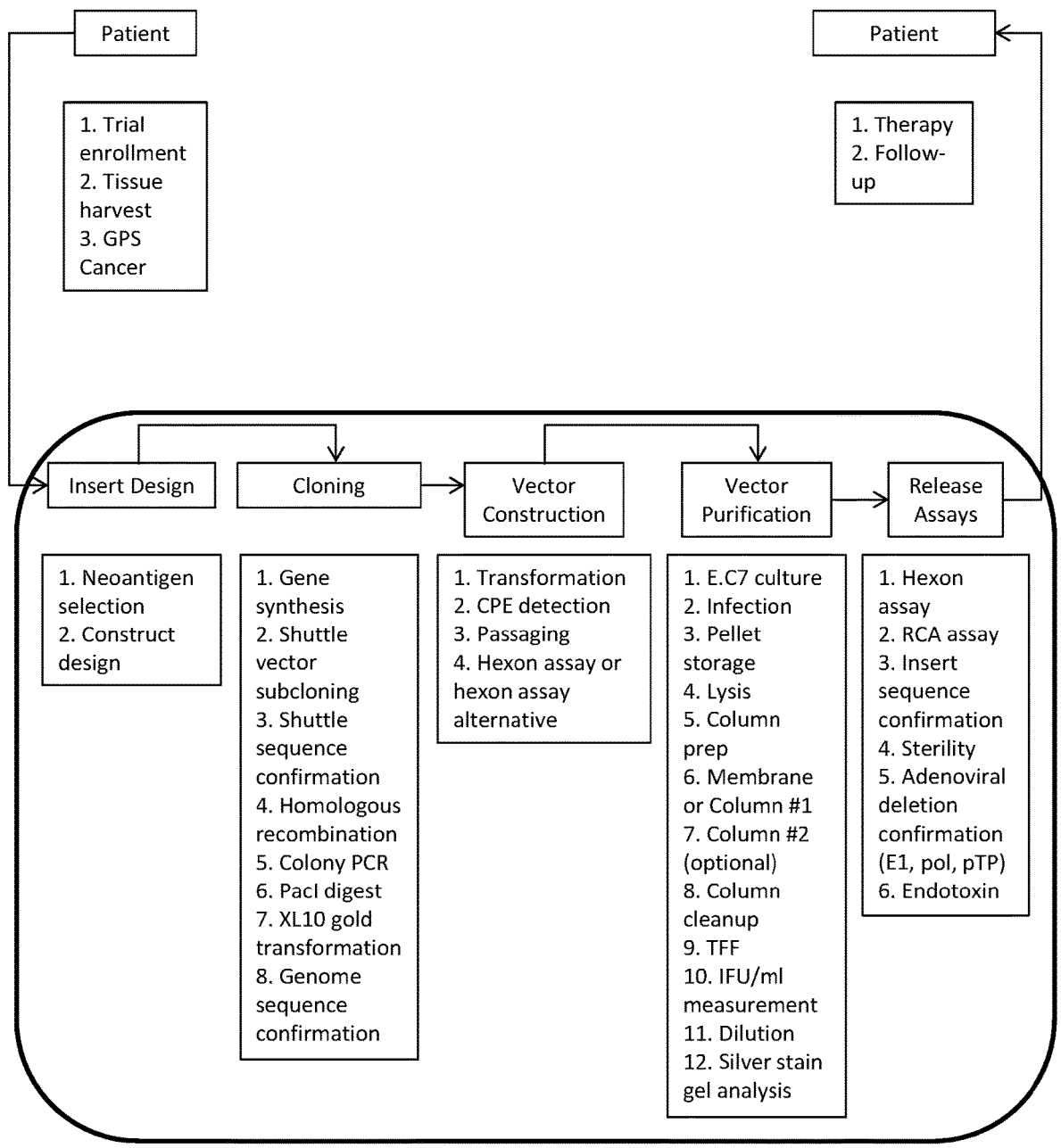
FIG. 1 illustrates a schematic showing each step in the process of manufacturing vaccines of the present disclosure. These steps include patient-specific identification of neo-antigens and/or neo-epitopes, design of a vector encoding for the neo-antigens and/or neo-epitope, cloning, vector construction, purification of the vector, release assays, and therapy with the resulting products in patients in need thereof.

The following passages describe different aspects of certain embodiments in greater detail. Each aspect may be combined with any other aspect or aspects unless clearly indicated to the contrary. In particular, any feature indicated as being preferred or advantageous may be combined with any other feature of features indicated as being preferred or advantageous.

Unless otherwise indicated, any embodiment can be combined with any other embodiment. A variety of aspects can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range as if explicitly written out. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. When ranges are present, the ranges include the range endpoints.

To address the inefficiencies in the manufacture of viral vectors, the present disclosure provides methods of improving rapid verification of infectious virions produced during manufacture. In particular, the present disclosure describes a hexon assay alternative, which confirms the presence of infectious virions via antibody-based detection of hexon expression in cells infected with a fully formed adenovirus. For example, in some embodiments the present disclosure describes methods of confirming the presence of infectious virions using an antibody-based, flow cytometry method of verifying hexon expression in suspension E.C7 cells. In other embodiments, the present disclosure describes methods of confirming the presence of infectious virions using an an antibody-based, flow cytometry method of verifying hexon expression in alternative suspension cell line (e.g., Jurkat, K562, or MOLT4) In other embodiments, the present disclosure describes methods of confirming the presence of infectious virions using an instrument, such as the BLItz® System from Pall, to quantify hexon expression. The methods of purification described in the present disclosure can, however, be broadly applied to other viral vectors for the production of clinical-grade vaccines.

Adenovirus Vectors

In general, adenoviruses are attractive for clinical because they can have a broad tropism, they can infect a variety of dividing and non-dividing cell types, and they can be used systemically as well as through more selective mucosal surfaces in a mammalian body. In addition, their relative thermostability further facilitates their clinical use. Adenoviruses (Ads) are a family of DNA viruses characterized by an icosahedral, non-enveloped capsid containing a linear double-stranded genome. Generally, adenoviruses are found as non-enveloped viruses comprising double-stranded DNA genome approximated ~30-35 kilobases in size. Of the human Ads, none are currently associated with any neoplastic disease, and only cause relatively mild, self-limiting illness in immunocompetent individuals. The first genes expressed by the virus are the E1 genes, which act to initiate high-level gene expression from the other Ad5 gene promoters present in the wild type genome. Viral DNA replication and assembly of progeny virions occur within the nucleus of infected cells, and the entire life cycle takes about 36 hr with an output of approximately $10^4$ virions per cell. The wild type Ad5 genome is approximately 36 kb, and encodes genes that are divided into early and late viral functions, depending on whether they are expressed before or after DNA replication. The early/late delineation is nearly absolute, since it has been demonstrated that super-infection of cells previously infected with an Ad5 results in lack of late gene expression from the super-infecting virus until after it has replicated its own genome. Without bound by theory, this is likely due to a replication dependent cis-activation of the Ad5 major late promoter (MLP), preventing late gene expression (primarily the Ad5 capsid proteins) until replicated genomes are present to be encapsulated. The composition and methods as described herein, in some embodiments, take advantage of feature in the development of advanced generation Ad vectors/vaccines. The linear genome of the adenovirus is generally flanked by two origins for DNA replication (ITRs) and has eight units for RNA polymerase II-mediated transcription. The genome carries five early units E1A, E1B, E2, E3, E4, and E5, two units that are expressed with a delay after initiation of viral replication (IX and IVa2), and one late unit (L) that is subdivided into L1-L5. Some adenoviruses can further encode one or two species of RNA called virus-associated (VA) RNA.

Adenoviruses that induce innate and adaptive immune responses in human patient are provided. By deletion or insertion of crucial regions of the viral genome, recombinant vectors are provided that have been engineered to increase their predictability and reduce unwanted side effects. In some aspects, there is provided an adenovirus vector comprising the genome deletion or insertion selected from the group consisting of: E1A, E1B, E2, E3, E4, E5, IX, IVa2, L1, L2, L3, L4, and L5, and any combination thereof.

Certain embodiments provide recombinant adenovirus vectors comprising an altered capsid. Generally, the capsid of an adenovirus primarily comprises 20 triangular facets of an icosahedron, each icosahedron containing 12 copies of hexon trimers. In addition, there are also other several additional minor capsid proteins, IIIa, VI, VIII, and IX.

Certain embodiments provide recombinant adenovirus vectors comprising one or more altered fiber proteins. In general, the fiber proteins, which also form trimers, are inserted at the 12 vertices into the pentameric penton bases. The fiber can comprise of a thin N-terminal tail, a shaft, and a knob domain. The shaft can comprise a variable number of β-strand repeats. The knob can comprise one or more loops of A, B, C, D, E, F, G, H, I, and/or J. The fiber knob loops can bind to cellular receptors. Certain embodiments provide adenovirus vectors to be used in vaccine systems for the treatment of cancers and infectious diseases.

Suitable adenoviruses that can be used with the present methods and compositions of the disclosure include but are not limited to species-specific adenovirus including human subgroups A, B 1, B2, C, D, E and F or their crucial genomic regions as provided herein, which subgroups can further be classified into immunologically distinct serotypes. Further, suitable adenoviruses that can be used with the present methods and compositions of the disclosure include, but are not limited to, species-specific adenovirus or their crucial genomic regions identified from primates, bovines, fowls, reptiles, or frogs.

Some adenoviruses serotypes preferentially target distinct organs. Serotypes such as AdHu1, AdHu2, and AdHu5 (subgenus C), generally effect the infect upper respiratory, while subgenera A and F effect gastrointestinal organs. Certain embodiments provide recombinant adenovirus vectors to be used in preferentially target distinct organs for the treatment of organ-specific cancers or organ-specific infectious diseases. In some applications, the recombinant adenovirus vector is altered to reduce tropism to a specific organ in a mammal. In some applications, the recombinant adenovirus vector is altered to increase tropism to a specific organ in a mammal.

The tropism of an adenovirus can be determined by their ability to attach to host cell receptors. In some instances, the process of host cell attachment can involve the initial binding of the distal knob domain of the fiber to a host cell surface molecule followed by binding of the RGD motif within the penton base with αV integrins. Certain embodiments provide recombinant adenovirus vectors with altered tropism such that they can be genetic engineered to infect specific cell types of a host. Certain embodiments provide recombinant adenovirus vectors with altered tropism for the treatment of cell-specific cancers or cell-specific infectious diseases. Certain embodiments provide recombinant adenovirus vectors with altered fiber knob from one or more adenoviruses of subgroups A, B, C, D, or F, or a combination thereof or the insertion of RGD sequences. In some applications, the recombinant adenovirus vectors comprising an altered fiber knob results in a vector with reduced tropism for one or more particular cell types. In some applications, the recombinant adenovirus vectors comprising an altered fiber knob results in a vector with enhanced tropism for one or more particular cell types. In some applications, the recombinant adenovirus vectors comprising an altered fiber knob results in a vector with reduced product-specific B or T-cell responses. In some applications, the recombinant adenovirus vectors comprising an altered fiber knob results in a vector with enhanced product-specific B or T-cell responses.

Certain embodiments provide recombinant adenovirus vectors that are coated with other molecules to circumvent the effects of virus-neutralizing antibodies or improve transduction in to a host cell. Certain embodiments provide recombinant adenovirus vectors that are coated with an adaptor molecule that aids in the attachment of the vector to a host cell receptor. By way of example an adenovirus vector can be coated with adaptor molecule that connects coxsackie Ad receptor (CAR) with CD40L resulting in increased transduction of dendritic cells (DCs), thereby enhancing immune responses in a subject. Other adenovirus vectors similarly engineered for enhancing the attachment to other target cell types are also contemplated.

Ad5 Vectors

Studies in humans and animals have demonstrated that pre-existing immunity against Ad5 can be an inhibitory factor to commercial use of Ad-based vaccines. The preponderance of humans have antibody against Ad5, the most widely used subtype for human vaccines, with two-thirds of humans studied having lympho-proliferative responses against Ad5. This pre-existing immunity can inhibit immunization or re-immunization using typical Ad5 vaccines and can preclude the immunization of a vaccine against a second antigen, using an Ad5 vector, at a later time. Overcoming the problem of pre-existing anti-vector immunity has been a subject of intense investigation. Investigations using alternative human (non-Ad5 based) Ad5 subtypes or even non-human forms of Ad5 have been examined. Even if these approaches succeed in an initial immunization, subsequent vaccinations can be problematic due to immune responses to the novel Ad5 subtype. To avoid the Ad5 immunization barrier, and improve upon the limited efficacy of first generation Ad5 [E1-] vectors to induce optimal immune responses, some embodiments relate to a next generation Ad5 vector based vaccine platform.

First generation, or E1-deleted adenovirus vectors Ad5 [E1-] are constructed such that a transgene replaces only the E1 region of genes. Typically, about 90% of the wild-type Ad5 genome is retained in the vector. Ad5 [E1-] vectors have a decreased ability to replicate and cannot produce infectious virus after infection of cells that do not express the Ad5 E1 genes. The recombinant Ad5 [E1-] vectors are propagated in human cells (e.g., 293 cells) allowing for Ad5 [E1-] vector replication and packaging. Ad5 [E1-] vectors have a number of positive attributes; one of the most important is their relative ease for scale up and cGMP production. Currently, well over 220 human clinical trials utilize Ad5 [E1-] vectors, with more than two thousand subjects given the virus subcutaneously, intra muscularly, or intravenously. Additionally, Ad5 vectors do not integrate; their genomes remain episomal. Generally, for vectors that do not integrate into the host genome, the risk for insertional mutagenesis and/or germ-line transmission is extremely low if at all. Conventional Ad5 [E1-] vectors have a carrying capacity that approaches 7 kb.

Ad5-based vectors with deletions of the E1 and the E2b regions (Ad5 [E1-, E2b-]), the latter encoding the DNA polymerase and the pre-terminal protein, by virtue of diminished late phase viral protein expression, provide an opportunity to avoid immunological clearance and induce more potent immune responses against the encoded tumor antigen transgene in Ad-immune hosts. The new Ad5 platform has additional deletions in the E2b region, removing the DNA polymerase and the preterminal protein genes. The Ad5 [E1-, E2b-] platform has an expanded cloning capacity that is sufficient to allow inclusion of many possible genes. Ad5 [E1-, E2b-] vectors have up to about 12 kb gene-carrying capacity as compared to the 7 kb capacity of Ad5 [E1-] vectors, providing space for multiple genes if needed. In some embodiments, an insert of more than 1, 2, 3, 4, 5, 6, 7, 8, 9, 10, or 11 kb is introduced into an Ad5 vector, such as the Ad5 [E1-, E2b-] vector. Deletion of the E2b region confers advantageous immune properties on the Ad5 vectors, often eliciting potent immune responses to target transgene antigens while minimizing the immune responses to Ad viral proteins.

In various embodiments, Ad5 [E1-, E2b-] vectors induce potent cell-mediated immunity (CMI), as well as antibodies against the vector expressed vaccine antigens even in the presence of Ad immunity. Ad5 [E1-, E2b-] vectors also have reduced adverse reactions as compared to Ad5 [E1-] vectors, in particular the appearance of hepatotoxicity and tissue damage. A key aspect of these Ad5 vectors is that expression of Ad late genes is greatly reduced. For example, production of the capsid fiber proteins could be detected in vivo for Ad5 [E1-] vectors, while fiber expression was ablated from Ad5 [E1-, E2b-] vector vaccines. The innate immune response to wild type Ad is complex. Proteins deleted from the Ad5 [E1-, E2b-] vectors generally play an important role. Specifically, Ad5 [E1-, E2b-] vectors with deletions of preterminal protein or DNA polymerase display reduced inflammation during the first 24 to 72 h following injection compared to Ad5 [E1-] vectors. In various embodiments, the lack of Ad5 gene expression renders infected cells invisible to anti-Ad activity and permits infected cells to express the transgene for extended periods of time, which develops immunity to the target.

Some embodiments contemplate increasing the capability for the Ad5 [E1-, E2b-] vectors to transduce dendritic cells, improving antigen specific immune responses in the vaccine by taking advantage of the reduced inflammatory response against Ad5 [E1-, E2b-] vector viral proteins and the resulting evasion of pre-existing Ad immunity.

Replication Defective Ad5 Vectors

Attempts to overcome anti-Ad immunity have included use of alternative Ad serotypes and/or alternations in the Ad5 viral capsid protein each with limited success and the potential for significantly altering biodistribution of the resultant vaccines. Therefore, a completely novel approach was attempted by further reducing the expression of viral proteins from the E1 deleted Ad5 vectors, proteins known to be targets of pre-existing Ad immunity. Specifically, a novel recombinant Ad5 platform has been described with deletions in the early 1 (E1) gene region and additional deletions in the early 2b (E2b) gene region (Ad5 [E1-, E2b-]). Deletion of the E2b region (that encodes DNA polymerase and the pre-terminal protein) results in decreased viral DNA replication and late phase viral protein expression. This vector platform can be used to induce CMI responses in animal models of cancer and infectious disease and more importantly, this recombinant Ad5 gene delivery platform overcomes the barrier of Ad5 immunity and can be used in the setting of pre-existing and/or vector-induced Ad immunity thus enabling multiple homologous administrations of the vaccine. In particular embodiments, some embodiments relate to a replication defective adenovirus vector of serotype 5 comprising a sequence encoding an immunogenic polypeptide. The immunogenic polypeptide can be a mutant, natural variant, or a fragment thereof.

Certain embodiments contemplate the use of E2b deleted adenovirus vectors, such as those described in U.S. Pat. Nos. 6,063,622; 6,451,596; 6,057,158; 6,083,750; and 8,298,549, which are each incorporated herein by reference in their entirety. The vectors with deletions in the E2b regions in many cases cripple viral protein expression and/or decrease the frequency of generating replication competent Ad (RCA). Propagation of these E2b deleted adenovirus vectors can be done utilizing cell lines that express the deleted E2b gene products. Such packaging cell lines are provided herein; e.g., E.C7 (formally called C-7), derived from the HEK-2p3 cell line.

Further, the E2b gene products, DNA polymerase and preterminal protein, can be constitutively expressed in E.C7, or similar cells along with the E1 gene products. Transfer of gene segments from the Ad genome to the production cell line has immediate benefits: (1) increased carrying capacity; and, (2) a decreased potential of RCA generation, typically requiring two or more independent recombination events to generate RCA. The E1, Ad DNA polymerase and/or preterminal protein expressing cell lines used in some embodiments can enable the propagation of adenovirus vectors with a carrying capacity approaching 13 kb, without the need for a contaminating helper virus. In addition, when genes critical to the viral life cycle are deleted (e.g., the E2b genes), a further crippling of Ad to replicate or express other viral gene proteins occurs. This can decrease immune recognition of infected cells, and extend durations of foreign transgene expression.

E1, DNA polymerase, and preterminal protein deleted vectors are typically unable to express the respective proteins from the E1 and E2b regions. Further, they can show a lack of expression of most of the viral structural proteins. For example, the major late promoter (MLP) of Ad is responsible for transcription of the late structural proteins L1 through L5. Though the MLP is minimally active prior to Ad genome replication, the highly toxic Ad late genes are primarily transcribed and translated from the mLP only after viral genome replication has occurred. This cis-dependent activation of late gene transcription is a feature of DNA viruses in general, such as in the growth of polyoma and SV-40. The DNA polymerase and preterminal proteins are important for Ad replication (unlike the E4 or protein IX proteins). Their deletion can be extremely detrimental to adenovirus vector late gene expression, and the toxic effects of that expression in cells such as APCs.

The adenovirus vectors can include a deletion in the E2b region of the Ad genome and, optionally, the E1 region. In some cases, such vectors do not have any other regions of the Ad genome deleted. The adenovirus vectors can include a deletion in the E2b region of the Ad genome and deletions in the E1 and E3 regions. In some cases, such vectors have no other regions deleted. The adenovirus vectors can include a deletion in the E2b region of the Ad genome and deletions in the E1, E3 and partial or complete removal of the E4 regions. In some cases, such vectors have no other deletions. The adenovirus vectors can include a deletion in the E2b region of the Ad genome and deletions in the E1 and/or E4 regions. In some cases, such vectors contain no other deletions. The adenovirus vectors can include a deletion in the E2a, E2b and/or E4 regions of the Ad genome. In some cases, such vectors have no other deletions. The adenovirus vectors can have the E1 and/or DNA polymerase functions of the E2b region deleted. In some cases, such vectors have no other deletions. The adenovirus vectors can have the E1 and/or the preterminal protein functions of the E2b region deleted. In some cases, such vectors have no other deletions. The adenovirus vectors can have the E1, DNA polymerase and/or the preterminal protein functions deleted. In some cases, such vectors have no other deletions. The adenovirus vectors can have at least a portion of the E2b region and/or the E1 region. In some cases, such vectors are not gutted adenovirus vectors. In this regard, the vectors can be deleted for both the DNA polymerase and the preterminal protein functions of the E2b region. The adenovirus vectors can have a deletion in the E1, E2b and/or 100K regions of the adenovirus genome. The adenovirus vectors can comprise vectors having the E1, E2b and/or protease functions deleted. In some cases, such vectors have no other deletions. The adenovirus vectors can have the E1 and/or the E2b regions deleted, while the fiber genes have been modified by mutation or other alterations (for example to alter Ad tropism). Removal of genes from the E3 or E4 regions can be added to any of the adenovirus vectors mentioned. In certain embodiments, adenovirus vectors can have a deletion in the E1 region, the E2b region, the E3 region, the E4 region, or any combination thereof. In certain embodiments, the adenovirus vector can be a gutted adenovirus vector.

Other regions of the Ad genome can be deleted. A "deletion" in a particular region of the Ad genome refers to a specific DNA sequence that is mutated or removed in such a way so as to prevent expression and/or function of at least one gene product encoded by that region (e.g., E2b functions of DNA polymerase or preterminal protein function). Deletions encompass deletions within exons encoding portions of proteins as well as deletions within promoter and leader sequences. A deletion within a particular region refers to a deletion of at least one base pair within that region of the Ad genome. More than one base pair can be deleted. For example, at least 20, 30, 40, 50, 60, 70, 80, 90, 100, 110, 120, 130, 140, or 150 base pairs can be deleted from a particular region. The deletion can be more than 150, 160, 170, 180, 190, 200, 250, or 300 base pairs within a particular region of the Ad genome. These deletions can prevent expression and/or function of the gene product encoded by the region. For example, a particular region of the Ad genome can include one or more point mutations such that one or more encoded proteins is non-functional. Such mutations include residues that are replaced with a different residue leading to a change in the amino acid sequence that result in a nonfunctional protein. Exemplary deletions or mutations in the Ad genome include one or more of E1a, E1b, E2a, E2b, E3, E4, L1, L2, L3, L4, L5, TP, POL, IV, and VA regions. Deleted adenovirus vectors can be made, for example, using recombinant techniques.

Ad vectors in certain embodiments can be successfully grown to high titers using an appropriate packaging cell line that constitutively expresses E2b gene products and products of any of the necessary genes that can be deleted. HEK-293-derived cells that not only constitutively express the E1 and DNA polymerase proteins, but also the Ad-preterminal protein, can be used. E.C7 cells can be used, for example, to grow high titer stocks of the adenovirus vectors.

To delete critical genes from self-propagating adenovirus vectors, proteins encoded by the targeted genes can first be coexpressed in HEK-293 cells, or similar, along with E1 proteins. For example, those proteins which are non-toxic when coexpressed constitutively (or toxic proteins inducibly-expressed) can be selectively utilized. Coexpression in HEK-293 cells of the E1 and E4 genes is possible (for example utilizing inducible, not constitutive, promoters). The E1 and protein IX genes, a virion structural protein, can be coexpressed. Further coexpression of the E1, E4, and protein IX genes is also possible. E1 and 100K genes can be expressed in trans-complementing cell lines, as can E1 and protease genes.

Cell lines co-expressing E1 and E2b gene products for use in growing high titers of E2b deleted Ad particles can be used. Useful cell lines constitutively express the approximately 140 kDa Ad-DNA polymerase and/or the approximately 90 kDa preterminal protein. Cell lines that have high-level, constitutive co-expression of the E1, DNA polymerase, and preterminal proteins, without toxicity (e.g., E.C7), are desirable for use in propagating Ad for use in multiple vaccinations. These cell lines permit the propagation of adenovirus vectors deleted for the E1, DNA polymerase, and preterminal proteins.

The recombinant Ad can be propagated using, for example, tissue culture plates containing E.C7 cells infected with Ad vector virus stocks at an appropriate multiplicity of infection (MOI) (e.g., 5) and incubated at 37° C. for 40-96 h.

In some embodiments, the successful production of infectious Ad5 virions can be confirmed using a hexon assay, which is an antibody-based cellular assay in which hexon-positive cells are manually counted by microscopy. For example, a small sample of E.C7 cells propagating the Ad5 vector can be analyzed for hexon expression using an antibody-based detection assay to quantify the infectious units (IFUs)/mL of Ad5 virions. Cells infected with virions can be capable of driving expression of hexon and hexon expression can be indicative of completion of the replication cycle of the virus. In some embodiments, hexon expression can occur if fully formed virions are present. In some embodiments, the hexon assay can be carried out via an anti-hexon antibody mediated immunostaining method. In some embodiments, after incubation of cells with the anti-hexon antibody, cells can be further incubated with a secondary antibody conjugated to horse radish peroxidase (HRP) enzyme. Cells can then be incubated with a DAB substrate. In some embodiments, the hexon assay can be carried out by manually counting dark cells by eye using a microscope. Cells that are darkened indicate accumulation of insoluble DAB peroxidase reaction products. However, the hexon assay can be an expensive assay due to costly reagents and can be labor intensive.

Thus, in some embodiments, the present disclosure provides a hexon assay alternative (see step 4 of vector construction in FIG. 1). In some embodiments, the hexon assay alternative is an antibody-mediated flow cytometry assay for detection of hexon expression in suspension E.C7 cells. For example, a small sample of E.C7 cells propagating the Ad5 vector can be sampled, lysed by freezing and thawing with a cryoprotectant, and concentrated by centrifugation. A small sample of the supernatant, comprising the Ad5 virions, can be serially diluted and incubated at various concentrations with a separate culture of suspension E.C7 cells in serum-free media. Suspension E.C7 cells can be incubated with Ad5 virions for 48 hours and can be further analyzed with a live/dead stain and with anti-hexon, fluorophore-labeled monoclonal antibody. Flow cytometry analysis can reveal the percentage of cells that are hexon positive, thereby indicating the infectivity of the Ad5 virions. In some embodiments, flow cytometry detection of hexon expression in suspension E.C7 cells can take up to 2-2.5 days.

In other embodiments, the hexon assay alternative can be an antibody-mediated flow cytometry assay for detection of hexon expression in suspension cells including, but not limited to, bone marrow-derived cells (e.g., K-562 cells), T-lymphoblast-derived cells (e.g., MOLT-4 cells), or T cell lymphoma (e.g., Jurkat E6-1 cells). Suspension cells (e.g., K-562 cells, MOLT-4 cells, or Jurkat E6-1 cells) can be transfected with plasmids shown in FIG. 3A and FIG. 3B and can, thus, express adenovirus 5 pol, pTP, E1a, and E1b, allowing for replication of Ad5 [E1-, E2b-] virions. Suspension cells (e.g., K-562 cells, MOLT-4 cells, or Jurkat E6-1 cells) can then be incubated with Ad5 virions obtained from E.C7 cells propagating the Ad5 vector by lysing and freeze/thaw techniques, as described above. Suspension cells (e.g., K-562 cells, MOLT-4 cells, or Jurkat E6-1 cells) can be incubated with Ad5 virions for 48 hours and can be further analyzed with a live/dead stain and with anti-hexon, fluorophore-labeled monoclonal antibody. Flow cytometry analysis can reveal the percentage of cells that are hexon positive, thereby indicating the infectivity of the Ad5 virions. In some embodiments, flow cytometry detection of hexon expression in suspension cells (e.g., K-562 cells, MOLT-4 cells, or Jurkat E6-1 cells) can take up to 2-2.5 days.

In still other embodiments, the hexon assay alternative can be hexon quantitation and correlation with infectivity via bio-layer interferometry (BLI) with the BLITZ® System or Octet® System from Pall FortéBio. In some embodiments, optical glass biosensors can be coated with an anti-hexon monoclonal antibody and a sample of clarified cell lysate from the E.C7 cells propagating the Ad5 vectors can be loaded onto the glass biosensor. Mass accumulation on the tip of the optical glass biosensor can be measured by the BLItz® or OCTET® System, thereby allowing for quantification of hexon-positive cells. In some embodiments, hexon quantification via bio-layer interferometry can be carried out in 5-30 minutes, 5-10 minutes, 10-15 minutes, 15-20 minutes, 20-25 minutes, or 25-30 minutes.

In some embodiments, any one of the above described hexon assay alternatives can be used to quantitate infectivity after E.C7 cells are transfected with any Ad5 vector of the present disclosure and have been propagated and passaged for 10 days.

The infected cells can be harvested, resuspended in 10 mM Tris-Cl (pH 8.0), and sonicated, and the virus can be purified by two rounds of cesium chloride density centrifugation. The virus containing band can be desalted over a column, sucrose or glycerol can be added, and aliquots can be stored at −80° C. However, the use of cesium chloride columns for density based purification of adenovirus can require long processing times and can be inefficient at purifying small-scale and large scale sample volumes. Moreover dialysis can be required to remove cesium chloride, which can be cytotoxic.

Thus, in other embodiments, the virus can be purified through an ion exchange based separation mechanism followed by a Source 30Q column (a Q sepharose column), which is a column purifier also based on an ion exchange mechanism. For example, in some embodiments, the ion exchange based separation mechanism can be a Q sepharose column. A Q sepharose column can contain a resin slurry with charged residues that bind the virus, while allowing undesired cellular components to pass. In some embodiments, the resin slurry is comprised of 30 μm polystyrene beads displaying quaternary cations. In some embodiments, the charged residues on the resin slurry are of an opposite charge to the virus in a first buffer. For example, in a first buffer with a particular ionic strength, the virus can be negatively charged and the charged residues on the resin slurry confer a positive charge, which can allow for the virus to bind the slurry. Subsequently, the virus can be eluted off the Q sepharose column by flowing through a second buffer with a different ionic strength that competes with the virus for binding to the Q sepharose column resin, causing the virus to elute. Finally, post-Q sepharose column purification, the virus can be passed through a Source 30Q column for a second round of purification, which can remove additional cellular proteins. In general, the Q sepharose column can be a polishing column, which removes residual cellular proteins not removed by a previous purification membrane or column.

In still other embodiments, in place of the Q sepharose column described above, virus vectors can be purified from infected E.C7 cells using a membrane (e.g. SARTOBIND® Q Membrane or MUSTANG® Q Membrane) that provides an ion exchange separation mechanism to bind undesirable components and purify intact viral vectors, including the adenovirus vectors of the present disclosure. For example, the SARTOBIND® Q Membrane or MUSTANG® Q Membrane can be used to purify the adenovirus vectors of the present disclosure. The SARTOBIND® Q Membrane or MUSTANG® Q Membrane adsorbs adenovirus due to its macro-porous structure which displays a positive ionic charge and has pore sizes of greater than 800 nm or greater than 3000 nm. Adenovirus, which is negatively charged at physiological pH can, thus, have a high binding capacity for the SARTOBIND® Q Membrane or MUSTANG® Q Membrane, while undesired cell lysates and proteins are filtered through. For example, the cell lysate containing the adenovirus can be loaded onto the SARTOBIND® Q Membrane or MUSTANG® Q Membrane in a salt buffer, also referred to herein as a "loading salt buffer." In some embodiments, the loading salt buffer, such as an NaCl salt buffer, can have an ionic strength of 300 mM-310 mM, 310 mM-320 mM, 320 mM-330 mM, 330 mM-340 mM, 340 mM-350 mM or 300 mM-350 mM. In some embodiments, the loading salt buffer, such as an NaCl salt buffer, can have an ionic strength of 325 mM NaCl. Upon completion of membrane purifying a cell lysate preparation, the adenovirus can be eluted off the SARTOBIND® Q Membrane or MUSTANG® Q Membrane by washing the membrane with a salt buffer, also referred to herein as a "elution salt buffer," at an ionic strength in which adenovirus becomes positively charged.

For example, in some embodiments, the elution salt buffer, such as an NaCl salt buffer, can have an ionic strength of 450 mM-540 mM, 450 mM-460 mM, 460 mM-470 mM, 470 mM-480 mM, 480 mM-490 mM, 490 mM-500 mM, 500 mM-510 mM, 510 mM-520 mM, 520 mM-530 mM, 530 mM-540 mM, 540 mM-550 mM, 550 mM-560 mM, 560 mM-570 mM, 570 mM-580 mM, 580 mM-590 mM, 590 mM-600 mM, 600 mM-610 mM, 610 mM-620 mM, 620 mM-630 mM, 630 mM-640 mM, 640 mM-650 mM, or 550 mM-650 mM. In some embodiments, the elution salt buffer, such as an NaCl salt buffer, can have an ionic strength of 450-540 mM NaCl. In some embodiments, the adenovirus can elute with an elution salt buffer of 450-540 mM NaCl. The loading or elution salt buffers can be a sodium chloride (NaCl)-based buffer. In some embodiments, use of the SARTOBIND® Q membrane or MUSTANG® Q Membrane can accelerate the purification process as compared to use of the Q Sepharose column. For example, the SARTOBIND® Q membrane or MUSTANG® Q Membrane can provide greater scalability and speed in purification of adenovirus from the cell lysate. Thus, in some embodiments, the SARTOBIND® Q membrane or MUSTANG® Q Membrane replaces the Q Sepharose column and a subsequent round of purification is performed using a Source 30Q column. In other embodiments, the SARTOBIND® Q membrane or MUSTANG® Q Membrane replaces the Q Sepharose column and the Source 30Q column and, thus, the adenovirus is purified in a single step. Vector purification steps of the present disclosure can include purification of cell lysate containing Ad5 vectors through a Q membrane (e.g., the SARTOBIND® Q membrane or MUSTANG® Q Membrane).

In some embodiments, the membrane purification step with the SARTOBIND® Q membrane or MUSTANG® Q Membrane is conducted using a fast protein liquid chromatography (FPLC) system, in which all aspects of the purification are computer controlled. For example, but adapting the Sartobind® Q membrane or MUSTANG® Q Membrane to an FPLC, the pump, buffer systems, and fraction collectors are all computer controlled.

In some embodiments, the membrane used is any ion exchange membrane. In some embodiments, the membrane has positively charged moieties (e.g., quarternary ammonium ligands) covalently conjugated to its inner surface. For example, the SARTOBIND® Q Membrane or MUSTANG® Q Membrane is a membrane with positively charged quarternary ammonium ligands covalently conjugated to its inner surface. These types of membranes can be used to purify negatively charged compositions of interest (e.g., Ad5). In other embodiments, the membrane has negatively charged moieties (e.g., sulfonic acid ligands) covalently conjugated to its inner surface. For example, the SARTOBIND® S Membrane or the MUSTANG® S Membrane is a membrane with negatively charged sulfonic acid ligands covalently conjugated to its inner surface. In some embodiments, the membrane used is a SARTOBIND® Q Membrane or MUSTANG® Q Membrane.

In some embodiments, the membrane purification involves lysing infected E.C7 cells to retrieve the Ad5 viral vectors of interest. For example, Ad5-expressing E.C7 cells can be lysed with an appropriate lysis buffer and then loaded onto a SARTOBIND® Q Membrane or MUSTANG® Q Membrane that has been equilibrated. After loading the cell lysate onto the SARTOBIND® Q Membrane or MUSTANG® Q Membrane and washing the membrane, Ad5 can be eluted with an appropriate buffer, for example, a solution of 650 mM NaCl. In some embodiments, the SARTOBIND® Q Membrane or MUSTANG® Q Membrane purification step takes 30 minutes to 2 hours, 30 minutes to 45 minutes, 30 minutes to 1 hour, 45 minutes to 1 hour, 1 hour to 1.5 hours, 1.5 hours to 2 hours, or 1 hour to 2 hours. In some embodiments, 50-200 mL of the cell lysate is filtered through the membrane purification system in any of the above described times. In some embodiments 1E13-1E14 virus particles (VPs)/mL of the neo-antigen vector is purified from the membrane purification system. In some embodiments, the SARTOBIND® Q Membrane or MUSTANG® Q Membrane purification step can process 1E8 to 4E9 cells/mL of membrane, wherein mL of membrane corresponds to the bed volume of the membrane, in 0.2-4 L of cell culture and retrieve 1E12 to 4.9E13 virus particles (VPs)/mL membrane.

Membrane purified adenovirus vectors can be further filtered through a Source 30Q column that has been equilibrated and Ad5 vectors can be eluted with an appropriate buffer, for example, a linear gradient of 0.15-1M NaCl. Subsequently, column purified adenovirus vectors can be subject to tangential flow filtration with a hollow-fiber (HF) membrane module using a KrosFlo instrument. Tangential flow filtration allows for concentration and buffer exchange of the purified, but diluted, adenovirus, by running the purified adenovirus under pressure against a buffer of choice. By passing the purified adenovirus through HF membranes, solutes are pushed out and exchanged. Adenovirus vectors can be stored in an appropriate storage buffer, for example, 2% 1M Tris at pH 8.0, 0.834% 3M NaCl, 5% glycerol and 92.166% $H_2O$.

In some embodiments, ion-exchange membranes of the present disclosure and purification columns of the present disclosure are disposed after a single use. In some embodiments, columns of the present disclosure are cleaned for further use. For example, cleanup of Q sepharose columns adapted to an FPLC instrument can be performed as follows. The sample pump inlet tubing can be cleaned with 0.5M NaOH by wetting a paper towel and cleaning the outside of the tubing, which was exposed to virus during sample load. The sample pump inlet can be placed in 0.5M NaOH. Columns can be cleaned with an all column cleaning run at 2 mL/min in upflow mode. For the Q sepharose column, 2-3 column volumes (CVs), for example 50 ml, of 0.5 M NaOH can be run from the sample pump, the run can be paused for 1 hour and the sample pump inlet can be placed into 2M NaCl, and 2-3 CVs, for example 50 mL, of 2 M NaOH can be run through the column without pausing. The sample pump inlet can be placed in $H_2O$ and 3-5 CVs, for example 150 mL, of $H_2O$ can be run through the column (Q sepharose or Source 30Q) until a conductivity detector is stable at less than 1 mS/cm. Source30Q columns can be cleaned by running the following solutions through the column from the sample pump, as described above, 30 mL of 0.5M NaOH, 30 mL of 2M NaCl, and 50 mL of $H_2O$. If the FPLC columns are not used for a period of greater than 10 days, they can be stored in 20% EtOH, which can be run through the columns and pumps at no more than 2 mL/min.

Virus can be placed in a solution designed to enhance its stability, such as A195, which can comprise 20 mM Tris, pH8.0, 25 mM NaCl, 2.5% glycerol. The titer of the stock can be measured (e.g., by measurement of the optical density at 260 nm of an aliquot of the virus after lysis). Plasmid DNA, either linear or circular, encompassing the entire recombinant E2b deleted adenovirus vector can be transfected into E.C7, or similar cells, and incubated at 37° C. until evidence of viral production is present (e.g., cytopathic effect). Conditioned media from cells can be used to infect more cells to expand the amount of virus produced before purification. Purification can be accomplished, for example, by two rounds of cesium chloride density centrifugation or selective filtration. Virus may be purified by chromatography using commercially available products or custom chromatographic columns.

The compositions as described herein can comprise enough virus to ensure that cells to be infected are confronted with a certain number of viruses. Thus, some embodiments provide a stock of recombinant Ad, such as an RCA-free stock of recombinant Ad. Viral stocks can vary considerably in titer, depending largely on viral genotype and the protocol and cell lines used to prepare them. Viral stocks can have a titer of at least about $10^6$, $10^7$, or $10^8$ infectious units (IFU)/mL, or higher, such as at least about $10^9$, $10^{10}$, $10^{11}$, or $10^{12}$ IFU/mL. Depending on the nature of the recombinant virus and the packaging cell line, a viral stock can have a titer of even about $10^{13}$ particles/ml or higher.

Polynucleotides and Variants Encoding Antigen Targets

Certain embodiments provide nucleic acid sequences, also referred to herein as polynucleotides that encode one or more target antigens of interest, or fragments or variants thereof. As such, some embodiments provide polynucleotides that encode target antigens from any source as described further herein and vectors comprising such polynucleotides and host cells transformed or transfected with such expression vectors. In order to express a desired target antigen polypeptide, nucleotide sequences encoding the polypeptide, or functional equivalents, can be inserted into an appropriate Ad vector (e.g., using recombinant techniques). The appropriate adenovirus vector can contain the necessary elements for the transcription and translation of the inserted coding sequence and any desired linkers. Standard methods can be used to construct these adenovirus vectors containing sequences encoding a polypeptide of interest and appropriate transcriptional and translational control elements. These methods can include in vitro recombinant DNA techniques, synthetic techniques, and in vivo genetic recombination, or any combination thereof.

Polynucleotides can comprise a native sequence (i.e., an endogenous sequence that encodes a target antigen polypeptide/protein/epitope or a portion thereof) or can comprise a sequence that encodes a variant, fragment, or derivative of such a sequence. Polynucleotide sequences can encode target antigen proteins. In some embodiments, polynucleotides represent a novel gene sequence optimized for expression in specific cell types that can substantially vary from the native nucleotide sequence or variant but encode a similar protein antigen.

Polynucleotides can comprise at least about 5, 10, 15, 20, 25, 30, 35, 40, 45, 50, 55, 60, 65, 70, 75, 80, 85, 90, 95, 100, 11, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900, 950, or 1000 or more contiguous nucleotides encoding a polypeptide (e.g., target protein antigens), and all intermediate lengths there between. "Intermediate lengths", in this context, refers to any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. A polynucleotide sequence can be extended at one or both ends by additional nucleotides not found in the native sequence encoding a polypeptide, such as an epitope or heterologous target protein. This additional sequence can consist of 1, 2, 3, 4, 5, 6, 7, 8, 9, 10, 11, 12, 13, 14, 15, 16, 17, 18, 19, or 20 nucleotides or more, at either end of the disclosed sequence or at both ends of the disclosed sequence.

The polynucleotides, regardless of the length of the coding sequence itself, can be combined with other DNA sequences, such as promoters, expression control sequences, polyadenylation signals, additional restriction enzyme sites, multiple cloning sites, other coding segments, and the like, such that their overall length can vary considerably. It is therefore contemplated that a nucleic acid fragment of almost any length can be employed, with the total length preferably being limited by the ease of preparation and use in the intended recombinant DNA protocol. Illustrative polynucleotide segments with total lengths of about 1000, 2000, 3000, 4000, 5000, 6000, 7000, 8000, 9000, 10,000, about 500, about 200, about 100, about 50 base pairs in length, and the like, (including all intermediate lengths) are contemplated to be useful in many embodiments.

A mutagenesis approach, such as site-specific mutagenesis, can be employed to prepare target antigen sequences. Specific modifications in a polypeptide sequence can be made through mutagenesis of the underlying polynucleotides that encode them. Site-specific mutagenesis can be used to make mutants through the use of oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. For example, a primer comprising from about 14 to about 25 nucleotides or so in length can be employed, with from about 5 to about 10 residues on both sides of the junction of the sequence being altered. Mutations can be made in a selected polynucleotide sequence to improve, alter, decrease, modify, or otherwise change the properties of the polynucleotide, and/or alter the properties, activity, composition, stability, or primary sequence of the encoded polypeptide.

Mutagenesis of polynucleotide sequences can be used to alter one or more properties of the encoded polypeptide, such as the immunogenicity of an epitope comprised in a polypeptide or the oncogenicity of a target antigen. Assays to test the immunogenicity of a polypeptide include, but are not limited to, T-cell cytotoxicity assays (CTL/chromium release assays), T-cell proliferation assays, intracellular cytokine staining, ELISA, ELISpot, etc. Other ways to obtain sequence variants of peptides and the DNA sequences encoding them can be employed. For example, recombinant vectors encoding the desired peptide sequence can be treated with mutagenic agents, such as hydroxylamine, to obtain sequence variants.

Polynucleotide segments or fragments encoding the polypeptides as described herein can be readily prepared by, for example, directly synthesizing the fragment by chemical means. Fragments can be obtained by application of nucleic acid reproduction technology, such as PCR, by introducing selected sequences into recombinant vectors for recombinant production.

A variety of vector/host systems can be utilized to contain and produce polynucleotide sequences. Exemplary systems include microorganisms such as bacteria transformed with recombinant bacteriophage, plasmid, or cosmid DNA vectors; yeast transformed with yeast vectors; insect cell systems infected with virus vectors (e.g., baculovirus); plant cell systems transformed with virus vectors (e.g., cauliflower mosaic virus, CaMV; tobacco mosaic virus, TMV) or with bacterial vectors (e.g., Ti or pBR322 plasmids); or animal cell systems.

Control elements or regulatory sequences present in an Ad vector can include those non-translated regions of the vector-enhancers, promoters, and 5' and 3' untranslated regions. Such elements can vary in their strength and specificity. Depending on the vector system and host utilized, any number of suitable transcription and translation elements, including constitutive and inducible promoters, can be used. For example, sequences encoding a polypeptide of interest can be ligated into an Ad transcription/translation complex consisting of the late promoter and tripartite leader sequence. Insertion in a non-essential E1 or E3 region of the viral genome can be used to obtain a viable virus which is capable of expressing the polypeptide in infected host cells. In addition, transcription enhancers, such as the Rous sarcoma virus (RSV) enhancer, can be used to increase expression in mammalian host cells.

Specific initiation signals can also be used to achieve more efficient translation of sequences encoding a polypeptide of interest (e.g., ATG initiation codon and adjacent sequences). Exogenous translational elements and initiation codons can be of various origins, both natural and synthetic. The efficiency of expression can be enhanced by the inclusion of enhancers which are appropriate for the particular cell system which is used. Specific termination sequences, either for transcription or translation, can also be incorporated in order to achieve efficient translation of the sequence encoding the polypeptide of choice.

A variety of protocols for detecting and measuring the expression of polynucleotide-encoded products (e.g., target antigens), can be used (e.g., using polyclonal or monoclonal antibodies specific for the product). Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide can be preferred for some applications, but a competitive binding assay can also be employed.

The Ad vectors can comprise a product that can be detected or selected for, such as a reporter gene whose product can be detected, such as by fluorescence, enzyme activity on a chromogenic or fluorescent substrate, and the like, or selected for by growth conditions. Exemplary reporter genes include green fluorescent protein (GFP), β-galactosidase, chloramphenicol acetyltransferase (CAT), luciferase, neomycin phosphotransferase, secreted alkaline phosphatase (SEAP), and human growth hormone (HGH). Exemplary selectable markers include drug resistances, such as neomycin (G418), hygromycin, and the like.

The Ad vectors can also comprise a promoter or expression control sequence. The choice of the promoter will depend in part upon the targeted cell type and the degree or type of control desired. Promoters that are suitable include, without limitation, constitutive, inducible, tissue specific, cell type specific, temporal specific, or event-specific. Examples of constitutive or nonspecific promoters include the SV40 early promoter, the SV40 late promoter, CMV early gene promoter, bovine papilloma virus promoter, and adenovirus promoter. In addition to viral promoters, cellular promoters are also amenable and useful in some embodiments. In particular, cellular promoters for the so-called housekeeping genes are useful (e.g., β-actin). Viral promoters are generally stronger promoters than cellular promoters. Inducible promoters can also be used. These promoters include MMTV LTR, inducible by dexamethasone, metallothionein, inducible by heavy metals, and promoters with cAMP response elements, inducible by cAMP, heat shock promoter. By using an inducible promoter, the nucleic acid can be delivered to a cell and will remain quiescent until the addition of the inducer. This allows further control on the timing of production of the protein of interest. Event-type specific promoters (e.g., HIV LTR) can be used, which are active or upregulated only upon the occurrence of an event, such as tumorigenicity or viral infection, for example. The HIV LTR promoter is inactive unless the tat gene product is present, which occurs upon viral infection. Some event-type promoters are also tissue-specific. Preferred event-type specific promoters include promoters activated upon viral infection.

Examples of promoters include promoters for α-fetoprotein, α-actin, myo D, carcinoembryonic antigen, VEGF-receptor; FGF receptor; TEK or tie 2; tie; urokinase receptor; E- and P-selectins; VCAM-1; endoglin; endosialin; αV-β3 integrin; endothelin-1; ICAM-3; E9 antigen; von Willebrand factor; CD44; CD40; vascular-endothelial cadherin; notch 4, high molecular weight melanoma-associated antigen; prostate specific antigen-1, probasin, FGF receptor, VEGF receptor, erb B2; erb B3; erb B4; MUC-1; HSP-27; int-1; int-2, CEA, HBEGF receptor; EGF receptor; tyrosinase, MAGE, IL-2 receptor; prostatic acid phosphatase, probasin, prostate specific membrane antigen, α-crystallin, PDGF receptor, integrin receptor, α-actin, SM1 and SM2 myosin heavy chains, calponin-h1, SM22 α-angiotensin receptor, IL-1, IL-2, IL-3, IL-4, IL-5, IL-6, IL-7, IL-8, IL-9, IL-10, IL-11, IL-12, IL-13, IL-14, immunoglobulin heavy chain, immunoglobulin light chain, and CD4.

Repressor sequences, negative regulators, or tissue-specific silencers can be inserted to reduce non-specific expression of the polynucleotide. Multiple repressor elements can be inserted in the promoter region. Repression of transcription is independent of the orientation of repressor elements or distance from the promoter. One type of repressor sequence is an insulator sequence. Such sequences inhibit transcription and can silence background transcription. Negative regulatory elements can be located in the promoter regions of a number of different genes. The repressor element can function as a repressor of transcription in the absence of factors, such as steroids, as does the NSE in the promoter region of the ovalbumin gene. These negative regulatory elements can bind specific protein complexes from oviduct, none of which are sensitive to steroids. Three different elements are located in the promoter of the ovalbumin gene. In some embodiments, oligonucleotides corresponding to portions of these elements can repress viral transcription of the TK reporter. For example, one such silencer element is TCTCTCCNA (SEQ ID NO: 1), which has a similar sequence identity as silencers that are present in other genes.

Elements that increase the expression of the desired target antigen can be incorporated into the nucleic acid sequence of the Ad vectors described herein. Exemplary elements include internal ribosome binding sites (IRESs). IRESs can increase translation efficiency. As well, other sequences can enhance expression. For some genes, sequences especially at the 5' end can inhibit transcription and/or translation. These sequences are usually palindromes that can form hairpin structures. In some cases, such sequences in the nucleic acid to be delivered are deleted. Expression levels of the transcript or translated product can be assayed to confirm or ascertain which sequences affect expression. Transcript levels can be assayed by any known method, including Northern blot hybridization, RNase probe protection and the like. Protein levels can be assayed by any known method, including ELISA.

Antigen-Specific Immunotherapies and Vaccines

Certain embodiments provide single antigen immunization against an antigen of interest utilizing such vectors and other vectors as provided herein. In some embodiments, the present disclosure provides prophylactic vaccines against an antigen of interest. In other embodiments, the compositions and methods provided herein can be used as a therapeutic vaccination in subjects with a condition, such as cancer. Therapeutic vaccination with any one of the disclosed vectors can lead to clinical responses, such as altered diseases progression or life expectancy.

Ad5 vector capsid interactions with DCs can trigger several beneficial responses, which can enhance the propensity of DCs to present antigens encoded by Ad5 vectors. For example, immature DCs, though specialized in antigen uptake, are relatively inefficient effectors of T-cell activation. DC maturation coincides with the enhanced ability of DCs to drive T-cell immunity. In some instances, the compositions and methods take advantage of an Ad5 infection resulting in direct induction of DC maturation Ad vector infection of immature bone marrow derived DCs from mice can upregulate cell surface markers normally associated with DC maturation (MHC I and II, CD40, CD80, CD86, and ICAM-1) as well as down-regulation of CD11c, an integrin down regulated upon myeloid DC maturation. In some instances, Ad vector infection triggers IL-12 production by DCs, a marker of DC maturation. Without being bound by theory, these events can possibly be due to Ad5 triggered activation of NF-κB pathways. Mature DCs can be efficiently transduced by Ad vectors, and do not lose their functional potential to stimulate the proliferation of naive T-cells at lower MOI, as demonstrated by mature CD83+ human DC (derived from peripheral blood monocytes). However, mature DCs can also be less vulnerable to infection than immature ones. Modification of capsid proteins can be used as a strategy to optimize infection of DC by Ad vectors, as well as enhancing functional maturation, for example using the CD40L receptor as a viral vector receptor, rather than using the normal CAR receptor infection mechanisms.

In some embodiments, the antigen targets are associated with benign tumors. In some embodiments, the antigens targeted are associated with pre-cancerous tumors.

In some embodiments, the antigens targeted are associated with carcinomas, in situ carcinomas, metastatic tumors, neuroblastoma, sarcomas, myosarcoma, leiomyosarcoma, retinoblastoma, hepatoma, rhabdomyosarcoma, plasmocytomas, adenomas, gliomas, thymomas, or osteosarcoma. In some embodiments, the antigens targeted are associated with a specific type of cancer such as neurologic cancers, brain cancer, thyroid cancer, head and neck cancer, melanoma, leukemia, acute lymphoblastic leukemia (ALL), acute myelogenous leukemia (AML), chronic myelogenous leukemia (CML), and chronic lymphocytic leukemia (CLL), non-Hodgkin's lymphoma, multiple myeloma, Hodgkin's disease, breast cancer, bladder cancer, prostate cancer, colorectal cancer, colon cancer, kidney cancer, renal cell carcinoma, pancreatic cancer, esophageal cancer, lung cancer, mesothelioma, ovarian cancer, cervical cancer, endometrial cancer, uterine cancer, germ cell tumors, testicular cancer, gastric cancer, or other cancers, or any clinical (e.g., TNM, Histopathological, Staging or Grading systems or a combination thereof) or molecular subtype thereof. In some embodiments, the antigens targeted are associated with a specific clinical or molecular subtype of cancer. By way of example, breast cancer can be divided into at least four molecular subtypes including Luminal A, Luminal B, Triple negative/basal-like, and HER2 type. By way of example, prostate cancer can be subdivided TNM, Gleason score, or molecular expression of the PSA protein.

As noted above, an adenovirus vector can comprise a nucleic acid sequence that encodes one or more target proteins or antigens of interest. In this regard, the vectors can contain nucleic acid encoding 1, 2, 3, 4, 5, 6, 7, 8, 9, 10, 11, 12, 13, 14, 15, 16, 17, 18, 19, 20 or more different target antigens of interest. The target antigens can be a full-length protein or can be a fragment (e.g., an epitope) thereof. The adenovirus vectors can contain nucleic acid sequences encoding multiple fragments or epitopes from one target protein of interest or can contain one or more fragments or epitopes from numerous different target proteins of interest. A target antigen can comprise any substance against which it is desirable to generate an immune response but generally, the target antigen is a protein. A target antigen can comprise a full-length protein, a subunit of a protein, an isoform of a protein, or a fragment thereof that induces an immune response (i.e., an immunogenic fragment). A target antigen or fragment thereof can be modified, e.g., to reduce one or more biological activities of the target antigen or to enhance its immunogenicity.

In certain embodiments, immunogenic fragments bind to an MHC class I or class II molecule. An immunogenic fragment can "bind to" an MHC class I or class II molecule if such binding is detectable using any assay known in the art. For example, the ability of a polypeptide to bind to MHC class I can be evaluated indirectly by monitoring the ability to promote incorporation of $^{125}$I labeled β-2-microglobulin (β-2m) into MHC class I/β2m/peptide heterotrimeric complexes. Alternatively, functional peptide competition assays that are known in the art can be employed. Immunogenic fragments of polypeptides can generally be identified using well known techniques. Representative techniques for identifying immunogenic fragments include screening polypeptides for the ability to react with antigen-specific antisera and/or T-cell lines or clones. An immunogenic fragment of a particular target polypeptide is a fragment that reacts with such antisera and/or T-cells at a level that is not substantially less than the reactivity of the full-length target polypeptide (e.g., in an ELISA and/or T-cell reactivity assay). In other words, an immunogenic fragment can react within such assays at a level that is similar to or greater than the reactivity of the full-length polypeptide. Such screens can be performed using methods known in the art.

In some embodiments, the viral vectors comprise heterologous nucleic acid sequences that encode one or more proteins, variants thereof, fusions thereof, or fragments thereof, that can modulate the immune response. In some embodiments, the viral vector encodes one or more antibodies against specific antigens, such as anthrax protective antigen, permitting passive immunotherapy. In some embodiments, the viral vectors comprise heterologous nucleic acid sequences encoding one or more proteins having therapeutic effect (e.g., anti-viral, anti-bacterial, anti-parasitic, or anti-tumor function). In some embodiments, the Second Generation E2b deleted adenovirus vectors comprise a heterologous nucleic acid sequence.

Target antigens include, but are not limited to, antigens derived from a variety of tumor proteins. In some embodiments, parts or variants of tumor proteins are employed as target antigens. In some embodiments, parts or variants of tumor proteins being employed as target antigens have a modified, for example, increased ability to effect and immune response against the tumor protein or cells containing the same. A vaccine can vaccinate against an antigen. A vaccine can also target an epitope. An antigen can be a tumor cell antigen. An epitope can be a tumor cell epitope. Such a tumor cell epitope can be derived from a wide variety of tumor antigens, such as antigens from tumors resulting from mutations, shared tumor specific antigens, differentiation antigens, and antigens overexpressed in tumors. Tumor-associated antigens (TAAs) can be antigens not normally expressed by the host; they can be mutated, truncated, misfolded, or otherwise abnormal manifestations of molecules normally expressed by the host; they can be identical to molecules normally expressed but expressed at abnormally high levels; or they can be expressed in a context or environment that is abnormal. Tumor-associated antigens can be, for example, proteins or protein fragments, complex carbohydrates, gangliosides, haptens, nucleic acids, other biological molecules or any combinations thereof.

Illustrative useful tumor proteins include, but are not limited to any one or more of, CEA, human epidermal growth factor receptor 1 (HER1), human epidermal growth factor receptor 2 (HER2/neu), human epidermal growth factor receptor 3 (HER3), human epidermal growth factor receptor 4 (HER4), MUC1, Prostate-specific antigen (PSA), PSMA, WT1, p53, MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-8, GAGE-3, GAGE-4, GAGE-5, GAGE-6, GAGE-7B, NA88-A, NY-ESO-1, MART-1, MC1R, Gp100, PSA, PSM, Tyrosinase, TRP-1, TRP-2, ART-4, CAMEL, CEA, Cyp-B, BRCA1, Brachyury, Brachyury (TIVS7-2, polymorphism), Brachyury (IVS7 T/C polymorphism), T Brachyury, T, hTERT, hTRT, iCE, MUC1, MUC1 (VNTR polymorphism), MUC1c, MUC1n, MUC2, PRAME, P15, RU1, RU2, SART-1, SART-3, AFP, β-catenin/m, Caspase-8/m, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, ETV6/AML, LDLR/FUT, Pml/RARα, HPV E6, HPV E7, and TEL/AML1.

In some embodiments, the viral vector comprises a target antigen sequence encoding a modified polypeptide selected from CEA, human epidermal growth factor receptor 1 (HER1), human epidermal growth factor receptor 2 (HER2/neu), human epidermal growth factor receptor 3 (HER3), human epidermal growth factor receptor 4 (HER4), MUC1, Prostate-specific antigen (PSA), PSMA (i.e., PSM), WT1, p53, MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-8, GAGE-3, GAGE-4, GAGE-5, GAGE-6, GAGE-7B, NA88-A, NY-ESO-1, MART-1, MC1R, Gp100, Tyrosinase, TRP-1, TRP-2, ART-4, CAMEL, Cyp-B, BRCA1, Brachyury, Brachyury (TIVS7-2, polymorphism), Brachyury (IVS7 T/C polymorphism), T Brachyury, T, hTERT, hTRT, iCE, MUC1 (VNTR polymorphism), MUC1c, MUC1n, MUC2, PRAME, P15, RU1, RU2, SART-1, SART-3, AFP, β-catenin/m, Caspase-8/m, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, ETV6/AML, LDLR/FUT, Pml/RARα, HPV E6, HPV E7, and TEL/AML1, wherein the polypeptide or a fragment thereof has at least 60%, 65%, 70%, 75%, 80%, 85%, 90%, 95%, 98%, 99%, 99.5%, or 99.9% identity to the corresponding native sequence.

Additional illustrative useful tumor proteins useful include, but are not limited to any one or more of alpha-actinin-4, ARTC1, CAR-ABL fusion protein (b3a2), B-RAF, CASP-5, CASP-8, beta-catenin, Cdc27, CDK4, CDKN2A, COA-1, dek-can fusion protein, EFTUD2, Elongation factor 2, ETV6-AML1 fusion protein, FLT3-ITD, FN1, GPNMB, LDLR-fucosyltransferase fusion protein, HLA-A2d, HLA-A1 ld, hsp70-2, KIAAO205, MART2, ME1, MUM-1f, MUM-2, MUM-3, neo-PAP, Myosin class I, NFYC, OGT, OS-9, p53, pml-RARalpha fusion protein, PRDX5, PTPRK, K-ras, N-ras, RBAF600, SIRT2, SNRPD1, SYT-SSX1- or -SSX2 fusion protein, TGF-betaRII, triosephosphate isomerase, BAGE-1, GnTVf, HERV-K-MEL, KK-LC-1, KM-HN-1, LAGE-1, MAGE-A9, MAGE-C2, mucink, NA-88, NY-ESO-1/LAGE-2, SAGE, Sp17, SSX-2, SSX-4, TAG-1, TAG-2, TRAG-3, TRP2-INT2g, XAGE-1b, gp100/Pmel17, Kallikrein 4, mammaglobin-A, Melan-A/MART-1, NY-BR-1, OA1, PSA, RAB38/NY-MEL-1, TRP-1/gp75, TRP-2, tyrosinase, adipophilin, AIM-2, ALDH1A1, BCLX (L), BCMA, BING-4, CPSF, cyclin D1, DKK1, ENAH (hMena), EP-CAM, EphA3, EZH2, FGF5, G250/MN/CAIX, IL13Ralpha2, intestinal carboxyl esterase, alpha fetoprotein, M-CSFT, MCSP, mdm-2, MMP-2, PBF, PRAME, RAGE-1, RGS5, RNF43, RU2AS, secernin 1, SOX10, STEAP1, survivin, Telomerase, and/or VEGF.

Tumor-associated antigens can be antigens from infectious agents associated with human malignancies. Examples of infectious agents associated with human malignancies include Epstein-Barr virus, *Helicobacter pylori,* Hepatitis B virus, Hepatitis C virus, Human heresvirus-8, Human immunodeficiency virus, Human papillomavirus, Human T-cell leukemia virus, liver flukes, and *Schistosoma haematobium.*

Infectious Disease-Associated Antigen Targets

Target antigens include, but are not limited to, antigens derived from any of a variety of infectious agents such as parasites, bacteria, virus, prions, and the like. An infectious agent can refer to any living organism capable of infecting a host. Infectious agents include, for example, bacteria, any variety of viruses, such as, single stranded RNA viruses, single stranded DNA viruses, fungi, parasites, and protozoa.

Examples of infectious disease associated target antigens that can be used with the compositions and the methods can be derived from the following: *Actinobacillus* spp., *Actinomyces* spp., Adenovirus (types 1, 2, 3, 4, 5, 6, and 7), Adenovirus (types 40 and 41), *Aerococcus* spp., *Aeromonas hydrophila, Ancylostoma duodenale, Angiostrongylus cantonensis, Ascaris lumbricoides, Ascaris* spp., *Aspergillus* spp., *Babesia* spp, *B. microti, Bacillus anthracis, Bacillus cereus, Bacteroides* spp., *Balantidium coli, Bartonella bacilliformis, Blastomyces dermatitidis, Bluetongue virus, Bordetella bronchiseptica, Bordetella pertussis, Borrelia afzelii, Borrelia burgdorferi, Borrelia garinii, Branhamella catarrhalis, Brucella* spp. (*B. abortus, B. canis, B. melitensis, B. suis*), *Brugia* spp., *Burkholderia, (Pseudomonas) mallei, Burkholderia (Pseudomonas) pseudomallei, California* serogroup, *Campylobacter fetus* subsp. *Fetus, Campylobacter jejuni, C. coli, C. fetus* subsp. *Jejuni, Candida albicans, Capnocytophaga* spp., *Chikungunya virus, Chlamydia psittaci, Chlamydia trachomatis, Citrobacter* spp., *Clonorchis sinensis, Clostridium botulinum, Clostridium difficile, Clostridium perfringens, Clostridium tetani, Clostridium* spp. (with the exception of those species listed above), *Coccidioides immitis,* Colorado tick fever virus, *Corynebacterium diphtheriae, Coxiella burnetii,* Coxsackievirus, Creutzfeldt-Jakob agent, Kuru agent, Crimean-Congo hemorrhagic fever virus, *Cryptococcus neoformans, Cryptosporidium parvum, Cytomegalovirus, Cyclospora cayatanesis,* Dengue virus (1, 2, 3, 4), Diphtheroids, Eastern (Western) equine encephalitis virus, Ebola virus, *Echinococcus granulosus, Echinococcus multilocularis, Echovirus, Edwardsiella tarda, Entamoeba histolytica, Enterobacter* spp., Enterovirus 70, *Epidermophyton floccosum, Ehrlichia* spp, *Ehrlichia sennetsu, Microsporum* spp. *Trichophyton* spp., Epstein-Barr virus, *Escherichia coli,* enterohemorrhagic, *Escherichia coli,* enteroinvasive, *Escherichia coli,* enteropathogenic, *Escherichia coli,* enterotoxigenic, *Fasciola hepatica, Francisella tularensis, Fusobacterium* spp., *Gemella haemolysans, Giardia lamblia,* Guanarito virus, *Haemophilus ducreyi, Haemophilus influenzae* (group b), Hantavirus, Hepatitis A virus, Hepatitis B virus, Hepatitis C virus, Hepatitis D virus, Hepatitis E virus, *Herpes simplex* virus, *Herpesvirus simiae, Histoplasma capsulatum,* Human coronavirus, Human immunodeficiency virus, Human papillomavirus, Human rotavirus, Human T-lymphotrophic virus, Influenza virus including H5N1, Junin virus/Machupo virus, *Klebsiella* spp., Kyasanur Forest disease virus, *Lactobacillus* spp., Lassa virus, *Legionella pneumophila, Leishmania major, Leishmania infantum, Leishmania* spp., *Leptospira interrogans, Listeria monocytogenes,* Lymphocytic choriomeningitis virus, Machupo virus, Marburg virus, Measles virus, *Micrococcus* spp., *Moraxella* spp., *Mycobacterium* spp. (other than *M. bovis, M. tuberculosis, M. avium, M. leprae), Mycobacterium tuberculosis, M. bovis, Mycoplasma hominis, M. orale, M. salivarium, M. fermentans, Mycoplasma pneumoniae, Naegleria fowleri, Necator americanus, Neisseria gonorrhoeae, Neisseria meningitides, Neisseria* spp. (other than *N. gonorrhoeae* and *N. meningitidis), Nocardia* spp., Norwalk virus, Omsk hemorrhagic fever virus, *Onchocerca volvulus, Opisthorchis* spp., Parvovirus B19, *Pasteurella* spp., *Peptococcus* spp., *Peptostreptococcus* spp., *Plasmodium falciparum, Plasmodium vivax, Plasmodium* spp., *Plesiomonas shigelloides,* Powassan encephalitis virus, *Proteus* spp., *Pseudomonas* spp. (other than *P. mallei, P. pseudomallei),* Rabies virus, Respiratory syncytial virus, Rhinovirus, *Rickettsia akari, Rickettsia prowazekii, R. Canada, Rickettsia rickettsii,* Rift Valley virus, Ross river virus/O'Nyong-Nyong virus, Rubella virus, *Salmonella choleraesuis, Salmonella paratyphi, Salmonella typhi, Salmonella* spp. (with the exception of those species listed above), *Schistosoma* spp., Scrapie agent, *Serratia* spp., *Shigella* spp., Sindbis virus, *Sporothrix schenckii,* St. Louis encephalitis virus, Murray Valley encephalitis virus, *Staphylococcus aureus, Streptobacillus moniliformis, Streptococcus agalactiae, Streptococcus faecalis, Streptococcus pneumoniae, Streptococcus pyogenes, Streptococcus salivarius, Taenia saginata, Taenia solium, Toxocara canis, T. cati, T. cruzi, Toxoplasma gondii, Treponema pallidum, Trichinella* spp., *Trichomonas vaginalis, Trichuris trichiura, Trypanosoma brucei, Trypanosoma cruzi, Ureaplasma urealyticum,* Vaccinia virus, Varicella-zoster virus, eastern equine encephalitis virus (EEEV), severe acute respiratory virus (SARS), Venezuelan equine encephalitis virus (VEEV), Vesicular stomatitis virus, *Vibrio cholerae,* serovar 01, *Vibrio parahaemolyticus,* West Nile virus, *Wuchereria bancrofti,* Yellow fever virus, *Yersinia enterocolitica, Yersinia pseudotuberculosis,* and *Yersinia pestis.* Target antigens can include proteins, or variants or fragments thereof, produced by any of the infectious organisms.

A number of viruses are associated with viral hemorrhagic fever, including filoviruses (e.g., Ebola, Marburg, and Reston), arenaviruses (e.g., Lassa, Junin, and Machupo), and bunyaviruses. In addition, phleboviruses, including, for example, Rift Valley fever virus, have been identified as etiologic agents of viral hemorrhagic fever. Etiological agents of hemorrhagic fever and associated inflammation can also include paramyxoviruses, particularly respiratory syncytial virus. In addition, other viruses causing hemorrhagic fevers in man have been identified as belonging to the following virus groups: togavirus (Chikungunya), flavivirus (dengue, yellow fever, Kyasanur Forest disease, Omsk hemorrhagic fever), nairovirus (Crimian-Congo hemorrhagic fever) and hantavirus (hemorrhagic fever with renal syndrome, nephropathic epidemia). Furthermore, Sin Nombre virus was identified as the etiologic agent of the 1993 outbreak of hantavirus pulmonary syndrome in the American Southwest.

Target antigens can include viral coat proteins, i.e., influenza neuraminidase and hemagglutinin, HIV gp160 or derivatives thereof, HIV Gag, HIV Nef, HIV Pol, SARS coat proteins, herpes virion proteins, WNV proteins, etc. Target antigens can also include bacterial surface proteins including pneumococcal PsaA, PspA, LytA, surface or virulence associated proteins of bacterial pathogens such as *Nisseria gonnorhea,* outer membrane proteins or surface proteases.

Personalized Tumor-Associated Antigens

In certain embodiments tumor-associated antigens used with the compositions and methods as described herein can be identified directly from an individual with a proliferative disease or cancer. In certain embodiments, cancers can include benign tumors, metastatic tumors, carcinomas, or sarcomas and the like. In some embodiments, a personalized tumor antigen comprises CEA characterized from a patient and further utilized as the target antigen as a whole, in part or as a variant.

In this regard, screens can be carried out using a variety of known technologies to identify tumor target antigens from an individual. For example, in one embodiment, a tumor biopsy is taken from a patient, RNA is isolated from the tumor cells and screened using a gene chip (for example, from AFFYMETRIX®, Santa Clara, Calif.) and a tumor antigen is identified. Once the tumor target antigen is identified, it can then be cloned, expressed, and purified using techniques known in the art.

This target antigen can then linked to one or more epitopes or incorporated or linked to cassettes or viral vectors described herein and administered to the patient in order to alter the immune response to the target molecule isolated from the tumor. In this manner, "personalized" immunotherapy and vaccines are contemplated in certain embodiments. Where cancer is genetic (i.e., inherited), for example, the patient has been identified to have a BRAC1 or BRAC2 mutation, the vaccine can be used prophylactically. When the cancer is sporadic this immunotherapy can be used to reduce the size of the tumor, enhance overall survival and reduce reoccurrence of the cancer in a subject.

Tumor Neo-Antigens

In some embodiments, the present disclosure provides identification of tumor neo-antigens to be used in a personalized vaccine to a subject in need thereof using any adenovirus vector described herein, such as the Ad5 [E1-, E2b-] virus vectors. Neo-antigens can also be referred to herein as "neo-epitopes." Tumor neo-antigens can result from various mutations, for example any category of DNA mutation, which can occur during tumorigenesis.

In some embodiments, neo-antigens can be more advantageous as a vaccine target as compared to other tumor antigens as described by Martin et al. (Ann Oncol. 2015 December; 26(12): 2367-2374). For example, T cells that are capable of targeting neo-antigens do not face tolerance and, thus, can be more cytotoxic against target neo-antigen bearing cancer cells and can be less affected by mechanisms of immune suppression. Because, neo-antigens result from mutations during tumorigenesis, neo-antigens can be wholly unique to cancer cells and can be absent from occurring in host cells. Incorporation of said neo-antigens in an effective adenovirus vector such as the Ad5 [E1-, E2b-] vectors described herein can, thus, be a powerful way of selectively vaccinating against tumors while minimizing off target cytotoxic effects on non-tumor host cells. Finally, multiple neo-antigens can be presented at the cell surface of tumor cells.

Mutations that can give rise to tumor neo-antigens, also referred to as somatic mutations, can be present at any residue in the neo-antigen. However, because neo-antigens must be (1) presented on an MHC molecule, such as MHC class I or MHC class II and (2) recognized as a complex with an MHC molecule by a T cell receptor (TCR), mutations that result in especially immunogenic neo-antigens can be located in residues that interact with an MHC molecule or interact with a TCR. Examples of mutations that can result in neo-antigens include non-synonymous mutations, read-through mutations, splice site mutations, chromosomal rearrangements, and frameshift mutations as described in detail in US Patent Application No. 20160331822. Sequencing techniques described in further detail below, can be used to identify said mutations in order to differentiate between tumor cells and host cell. Neo-antigens of the present application can also include mutations that are known to be drivers of tumor genesis, for example any of those described in the Catalogue of Somatic Mutations in Cancer (COSMIC) database (http://cancer.sanger.ac.uk/cosmic). Neo-antigens can be derived from driver and passenger genes as described by Martin et al. (Ann Oncol. 2015 December; 26(12): 2367-2374) and can be present in several different types of tumors.

Sequencing Methods

In some embodiments, methods and assays for identifying the neo-antigens described herein are provided. In some embodiments, the present disclosure provides sequencing techniques, such as next-generation sequencing techniques, to identify tumor neo-epitopes associated with cancer cells. Processed tissue samples are DNA or RNA sequencing to identify mutations that are unique to tumor neo-antigens, which are distinct from host cells. Sequencing can be performed on patient-derived samples to identify possible neo-epitopes to target utilizing an adenovirus vector-based vaccine. For example, in some embodiments, tissue from a subject in need thereof is obtained and processed for sequencing analysis. Sequencing analysis can be combined with genomics, bioinformatics, and immunological approaches to identify mutant tumor associated antigens and epitopes.

In some embodiments, sequencing methods and assays for obtaining a sequence-verified neo-antigen vector are described herein. For example, any sequencing method described herein can be used to analyze the sequence of a replication-defective vector of the present disclosure with or without a desired neo-antigen construct inserted into the vector. Said sequencing of the replication-defective vector can confirm that the desired construct was designed and produced. Said sequencing can be performed at any step of producing a sequence-verified neo-antigen vector. For example, in some embodiments, sequencing of a neo-antigen vector comprising a neo-antigen sequence and a sequence for an Ad5 [E1-, E2b-] vector of the present disclosure, to obtain a sequence-verified neo-antigen vector, can be performed following homologous recombination of the neo-antigen into the vector, following membrane purification of the vector, or any combination thereof. The goal of obtaining a sequence-verified neo-antigen vector can be to confirm that a polynucleotide sequence of a final packaged virion is 100% identical to a polynucleotide sequence of a shuttle plasmid, to confirm that a polynucleotide sequence of a final packaged virion is 100% identical to a polynucleotide sequence of the vector and neo-antigen following homologous recombination, to confirm that a polynucleotide sequence of the vector comprises a deletion in an E1 region, an E2 region, an E2b region, an E3 region, an E4 region, or any combination thereof of a replication defective viral vector, to confirm that a polynucleotide sequence does not comprise any unintentional sequencing errors, to confirm that a polynucleotide sequence that comprises the vector and neo-antigen does not comprise one or more contaminating sequences, to confirm that a sequence of a neo-antigen produced after passaging the cells, or any combination thereof. In some embodiments, the sequencing methods of the present disclosure can be used to obtain a sequence-verified neo-antigen vector that can be used as a personalized cancer vaccine in a subject in need thereof. Sequence verification can be a pivotal step in producing personalized cancer vaccines, particularly for neo-antigens, which are specific to patients and are not commonly characterized in the art. Thus, the methods described herein can be used to obtain sequence-verified neo-antigen vectors, which can have superior efficacy and lower off-target effects as compared to non-sequence verified neo-antigen vectors, which may encode for erroneous or incorrect moieties. In some embodiments, any next generation sequencing (NGS) technique used herein to obtain the sequence-verified neo-antigen vector confirms that sequence-verified neo-antigen vector has at least 90%, 92%, 95%, 97%, 99%, or 99.5% sequence identity to the expected sequence. NGS techniques of the present disclosure are described in further detail below.

In some embodiments, the tissue obtained from a subject can be analyzed by any sequencing technique, including whole exome sequencing or whole genome sequencing. Non sequencing techniques can also be used to supplement sequencing data in order to identify neo-antigens with high binding affinity for MHC. For example, computer algorithms can be used to predict binding affinity of a given neo-antigen to MHC. In some embodiments, MHC multimer screens and functional T cell assays can be used to assess the immunogenicity of an identified neo-antigen. Any next-generation sequencing (NGS) method can be used herein to sequence a tumor tissue sample obtained from a subject. Said NGS methods can include, but are not limited to, those described below.

In some embodiments, GPS CANCER™ can be used to sequence-verify neo-antigen vectors or to sequence neo-antigens, as described above. GPS CANCER™ can include mass spectrometry, whole genome (DNA) sequencing, and whole transcriptome (RNA) sequencing. GPS CANCER™ sequencing methods and analyses can be used to provide personalized treatment strategies for a subject in need thereof, as further described at www.gpscancer.com.

Tumor neo-antigens can be identified using standard next-generation sequencing (NGS) methods including, but not limited to, genome sequencing and resequencing, RNA-sequencing, and ChIP sequencing.

Said techniques can be used identify mutations, such as missense mutations or frameshift mutations, in tumor cells as compared to host cells. DNA mutations can be identified using massively parallel sequencing (MPS) as described by Gubin et al. (J Clin Invest. 2015 Sep. 1; 125(9): 3413-3421) and Simpson et al. (Nat Rev Cancer. 2005 August; 5(8): 615-25). RNA can also be analyzed by first obtaining corresponding cDNA and sequencing said cDNA. In some embodiments, exome-capture can be used to sequence and identify tumor neo-antigen genes as described in Gubin et al. (J Clin Invest. 2015 Sep. 1; 125(9): 3413-3421) by comparison of the resulting sequencing data to normal cells, which can serve as a reference sequence.

Further assays that can be used to identify tumor neo-antigens include, but are not limited to, proteomics (e.g., protein sequencing by tandem mass spectrometry (MS/MS) or meta-shotgun protein sequencing), array hybridization, solution hybridization, nucleic amplification, polymerase chain reaction, quantitative PCR, RT-PCR, in situ hybridization, Northern hybridization, hybridization protection assay (HPA) (GenProbe), branched DNA (bDNA) assay (Chiron), rolling circle amplification (RCA), single molecule hybridization detection (US Genomics), Invader assay (ThirdWave Technologies), and/or Oligo Ligation Assay (OLA), hybridization, and array analysis as described in US20170211074, which is incorporated herein by reference.

In some embodiments, a panomics-based test is performed to compare sequencing data between a tumor sample and a normal reference samples. Said panomics-based tests can comprise analyzing the whole genome, single nucleotide variances (SNVs), copy number variances, insertions, deletions, rearrangements, or any combination thereof. Samples that can be sequenced for identification of tumor neo-antigens can be any sample from a subject. Said samples can be extracted for DNA or RNA. In some embodiments, samples can be formalin fixed paraffin embedded (FFPE) or freshly frozen. In some embodiments, the RainStorm (Raindance Technologies) system or molecular inversion probes (MIP) can be used for DNA extraction from FFPE samples. In some embodiments, the sample can be whole blood. In some embodiments, the sample is a solid tumor tissue sample or a liquid tumor sample. Samples can be enriched, for example, using laser microdissection. The TRUSEQ™ DNA Sample Preparation Kit and the Exome Enrichment Kit TRUSEQ™ Exome Enrichment Kit can be used for sample preparation and enrichment prior to sequencing. In some embodiments, enrichment can comprise PCR-amplicon based methods or hybridization capture methods as described in Meldrum et al. (Clin Biochem Rev. 2011 November; 32(4): 177-195). In some embodiments, microfluidics-based methods can be used for PCR-based enrichment. For example, the Fluidigm system can be used to carry out multiple parallel PCR reactions.

In some embodiments, any suitable sequencing method can be used including, but not limited to, the classic Sanger sequencing method, high-throughput sequencing, pyrosequencing, sequencing-by-synthesis, single-molecule sequencing, nanopore sequencing, sequencing-by-ligation, sequencing-by-hybridization, RNA-Seq (Illumina), Digital Gene Expression (Helicos), next generation sequencing, single molecule sequencing by synthesis (SMSS) (Helicos), massively-parallel sequencing, clonal single molecule Array (Solexa), shotgun sequencing, Maxim-Gilbert sequencing, primer walking, next-generation sequencing, and any other sequencing methods known in the art. In some embodiments, sequencing methods and assays for obtaining a sequence-verified neo-antigen vector are carried out using Sanger sequencing to verify the insert and polymerase chain reaction (PCR) to test for mutations. In some embodiments, Sanger sequencing confirms that the neo-antigen vector obtained through the methods of making described herein has 97%, 98%, 99%, 99.1%, 99.2%, 99.3%, 99.4%, 99.5%, 99.6%, 99.7%, 99.8%, or 99.9% sequence identity to the expected sequence.

In some instances, next-generation sequencing, or "NGS," can be used to sequence a molecule described herein. NGS techniques can include all novel high throughput sequencing technologies which, in contrast to the "conventional" sequencing methodology known as Sanger chemistry, read nucleic acid templates randomly in parallel along the entire genome by breaking the entire genome into small pieces.

Any NGS technique can be used to analyze the whole genome, exomes, transcriptomes, and/or methylomes, as described in WO2016128376 A1. Said NGS techniques can be carried out in less than 2 weeks, less than 1 week, less than 6 days, less than 5 days, less than 4 days, less than 3 days, less than 2 day, or less than 1 day. Commercially NGS platforms that can be used to sequence for neo-antigens of the present disclosure are described by Zhang et al. (J Genet Genomics. Author manuscript; available in PMC 2011 Apr. 13).

NGS methods used herein can include any method described in Masoudi-Nejad, Ali, Zahra Narimani, and Nazanin Hosseinkhan. Next generation sequencing and sequence assembly: methodologies and algorithms. Vol. 4. Springer Science & Business Media, 2013; Buermans et al., "Next Generation sequencing technology: Advances and applications," *Biochimica et Biophysica Acta,* 1842:1931-1941, 2014.; and by Liu et al., Comparison of Next-Generation Sequencing Systems. *Journal of Biomedicine and Biotechnology,* 11 pages, 2012. NGS methods used herein can also include those described in US20160125129, each of which is incorporated herein by reference.

For example, in some embodiments, sequencing-by-synthesis (Solexa, now Illumina) can be performed using the Illumina/Solexa Genome ANALYZER™ and the Illumina HiSeq 2000 Genome Analyze.

In some embodiments, sequencing-by-ligation can be performed using SOLID™ platform of Applied Biosystems (Life Technologies) or the POLONATOR™ G.007 platform of Dover Systems (Salem, N.H.).

In some embodiments, single-molecule sequencing can be performed using the PacBio RS system of Pacific Biosciences (Menlo Park, Calif.), the HELISCOPE™ platform of Helicos Biosciences (Cambridge, Mass.), a fluorescence based systems from Visigen Biotechnology (Houston, Tex.), U.S. Genomics (GENEENGINE™), or Genovoxx (ANYGENE™).

In some embodiments, nanotechnology based single-molecule sequencing can be performed using GRIDON™ platform, hybridization-assisted nano-pore sequencing (HANS™) platforms, ligase-based DNA sequencing platform referred to as combinatorial probe-anchor ligation (CPAL™), and electron microscopy.

In some embodiments, the NGS method is ion semiconductor sequencing, which can be performed using Ion Torrent Systems.

Further methods are described in Teer et al. (Hum Mol Genet. 2010 Oct. 15; 19(R2):R145-51), Hodges et al. (Nat Genet. 2007 December; 39(12):1522-7), and Choi et al. (Proc Natl Acad Sci USA. 2009 Nov. 10; 106(45):19096-101).

Commercial kits for DNA sample preparation and subsequent exome capture are also available: for example, Illumina Inc. (San Diego, Calif.) offers the TruSeq™ DNA Sample Preparation Kit and the Exome Enrichment Kit TRUSEQ™ Exome Enrichment Kit.

In some embodiments, RNA sequencing can be used to identify tumor neo-antigens. RNA sequencing technologies can include any high-throughput sequencing method, for example, Illumina IG, Applied Biosystems SOLiD and Roche 454 Life Science systems, or a Helicos Biosciences tSMS system as described in Wang et al. (Nat Rev Genet. 2009 January; 10(1): 57-63). In some embodiments, extracted RNA can be converted to cDNA and subsequently sequenced at read lengths of 30-400 base pairs.

High-throughput sequencing methods can also be employed to characterize short stretches of sequence contiguity and genomic variation. U.S. Pat. No. 9,715,573 (Dovetail Genomics, LLC) discloses methods for rapid paired and/or grouped sequence reads, which can be used to assess sequence contiguity at the chromosomal level.

Identification of Tumor Neo-Antigens and Neo-Epitopes

In some embodiments, sequencing analysis can be used to identify neo-antigens. The neo-antigen can be an 8 mer to a 50 mer. In other embodiments, the neo-antigen can be up to a 25 mer. Identified neo-antigens can be further analyzed for their affinity for binding HLA molecules of a subject. As described above, highly immunogenic neo-antigens can have high affinity for MHC (HLA in humans) molecules. In some embodiments, the present disclosure provides neo-antigen inserts, which can comprise one or more than one neo-antigen sequences, a linker, a tag, and other factors, and can therefore be up to 3 kilobases.

In some embodiments, the HLA type of a subject is identified and computer prediction algorithms are used to model mutations in neo-antigens that can result in high affinity for binding HLA and/or MEW molecules. Tools to predict neo-antigen binding to MEW molecules can include any of those available at http://cancerimmunity.org/resources/webtools, including but not limited to, PAProC, NetChop, MAPPP, TAPPred, RankPep, MHCBench, HLA Peptide Binding Predictions, PREDEP, nHLAPred-I, ProPred-1, SVMHC, EPIPREDICT, ProPred, NetMHC, NetMHCII, NetMHCpan, SMM, POPI, OptiTope, Mosaic Vaccine Tool Suite, HLABinding, Prediction of Antigenic Determinants, ANTIGENIC, BepiPred, DiscoTope, ElliPro, Antibody Epitope Prediction, CTLPred, NetCTL, MHC-I processing predictions, Epitope Cluster Analysis, Epitope Conservancy Analysis, VaxiJen, or combinations thereof. Programs such as SYFPEITHI, as described in Rammensee et al. (Immunogenetics. 1999 November; 50(3-4):213-9), Rankpep, as described in Reche et al. (Hum Immunol. 2002 September; 63(9):701-9), or BIMAS, as described in Parker et al (J Immunol. 1994 Jan. 1; 152(1):163-75) can also be used. In some embodiments, neo-antigens can also be identified using the Immune Epitope Database and Analysis Resource (IEDB), as described in Vita et al. (Nucleic Acids Res. 2015 January; 43(Database issue):D405-12). In some embodiments, said algorithms can predict peptide binding to MHC class I variants using artificial neural networks (ANN). These algorithms can yield IC50 values as a metric of neo-antigen binding to MHC. NetMHC (Lundegaard et al. Nucleic Acids Res. 2008 Jul. 1; 36(Web Server issue): W509-W512. Published online 2008 May 7), or SMM (Peters et al. BMC Bioinformatics. 2005 May 31; 6:132) and SMMPMBEC (Kim et al. BMC Bioinformatics. 2009 Nov. 30; 10:394) can also be used. MHC tetramer based assays can also be used to identify tumor neo-antigens with high binding affinity for MHC molecules as described in Lu et al. (Semin Immunol. 2016 February; 28(1): 22-27). In some embodiments, SNPs can be removed from neo-antigens.

In some embodiments, tumor neo-antigens can also be identified by pulsing antigen presenting cells with relatively long synthetic peptides that encompass minimal T cell epitopes, as described by Lu et al. (Semin Immunol. 2016 February; 28(1): 22-27). In other embodiments, tumor neo-antigens can also be identified using tandem minigene screening or sequencing analysis of the whole-exome or the transcriptome, as described by Lu et al.

Tumor Neo-Epitope Prioritization

In some embodiments, methods are provided for prioritizing tumor neo-antigens that can stimulate robust immune response after vaccination in an Ad5 [E1-, E2b-] viral vector of the present disclosure. For example, tumor neo-antigens identified by sequencing methods can be subsequently classified and prioritized by MHC binding affinity. Tumor neo-antigens can be further classified and prioritized by epitope abundance, as determined by mass spectrometry, RNA expression levels, or RNA sequencing. Tumor neo-antigens can be further classified and prioritized by antigen processing, including antigen degradation and transport to MHC processing pathways.

Neo-antigen prioritization can be further refined by eliminating false positives and can be further subject to algorithms described in Gubin et al. (J Clin Invest. 2015 Sep. 1; 125(9): 3413-3421), including NetChop, NetCTL, and NetCTLpan (Nielsen M, et al. Immunogenetics, 2005; 57(1-2):33-41, Peters B, et al. J. Immunol., 2003; 171(4):1741-1749).

MHC Class II binding affinities can be assessed using prediction algorithms such as those described in Gubin et al. (J Clin Invest. 2015 Sep. 1; 125(9): 3413-3421), including TEPITOPE (Hammer J, et al. J. Exp. Med., 1994; 180(6): 2353-2358), netMHCII (Nielsen M, et al. BMC Bioinformatics. 2009; 10:296), and SMM-align (Nielsen M, et al. BMC Bioinformatics 2007; 8:238). Known programs such as the NetMHCpan program can be used to identify neo-antigens with high binding affinity for MHC.

In some embodiments, the affinity of a neo-antigen of the present disclosure for an MHC molecules can be less than 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 400, 450, 500 nmol/L. In some embodiments, a neo-antigen that has strong affinity for MHC can have an IC50 value of less than 50 nmol/L. In some embodiments, a neo-antigen that has moderate affinity for MHC can have an IC 50 value from 50 to 150 nmol/L. In some embodiments, a neo-antigen that has weak affinity for MHC can have an IC50 value from 150 to 500 nmol/L. In some embodiments, a neo-antigen that has low or no affinity for MHC can have an IC50 value greater than 500 nmol/L.

In some embodiments, functional T cell responses can be further examined to prioritize neo-antigens. For example, neo-antigen pulsed antigen presenting cells can be co-cultured with CD4+ or CD8+ T cells and T-cell proliferation and cytokine release can be examined. Neo-antigens that elicit the highest functional T cell response can be prioritized for incorporation into a vector of the present disclosure In some embodiments, the present disclosure provides methods of making and administering an individual, personalized neo-antigen/neo-epitope vaccine. For example, the present disclosure provides methods for obtaining a sample from a subject and analyzing the sample for the presence of tumor neo-epitopes or neo-antigens that are unique to that subject or to a subset of individuals. The tumor neo-epitopes or neo-antigens can be then sequenced and inserted into a vector of the present disclosure as shown in FIG. 1 at the insert design stage. Vectors are then subject to the manufacturing process of the present disclosure, which includes the step of utilizing a SARTOBIND® Q Membrane for purification, yielding efficient and high purity adenovirus vectors encoding for the neo-antigen or neo-epitope of interest. In some embodiments, the resulting neo-antigen vaccine can be sequence verified using high throughput sequencing methods, such as any next generation sequencing technique. The resulting neo-antigen/neo-epitope personalized vaccine can be administered back to the subject in need thereof.

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application.

Example 1

Antibody-Mediated Flow Cytometry Detection of Hexon Expression in Suspension E.C7 Cells This example describes antibody-mediated flow cytometry detection of hexon expression in suspension E.C7 cells to verify production of infectious adenovirus virions and to quantify infectious units (IFUs)/mL. E.C7 cells were transferred to serum free media and grown in suspension for one day, then transferred to 96-well plates and infected with a dilution series of adenovirus-containing media. E.C7 cells were cultured with adenovirus-containing media for 48 hours after which cells were centrifuged. The cell pellet was resuspended and stained for live cells, fixed, permeabilized, and stained for hexon with a fluorophore-conjugated monoclonal antibody against hexon protein. Cells were analyzed for fluorescence corresponding to hexon protein via flow cytometry.

Figure 2A:
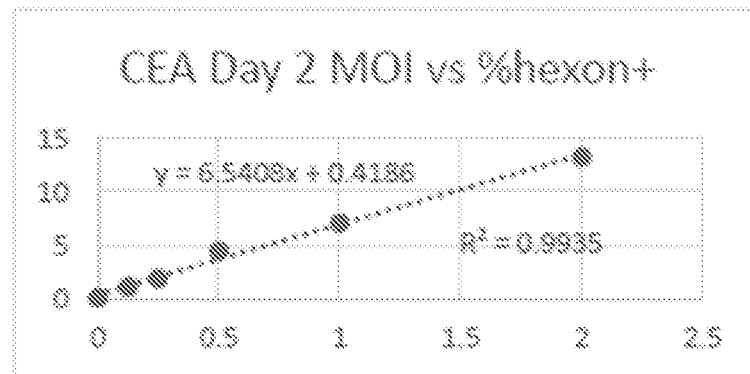
FIGS. 2A-2C show results from flow cytometry-based detection of hexon protein in E.C7 infected cells.
Figure 2B:
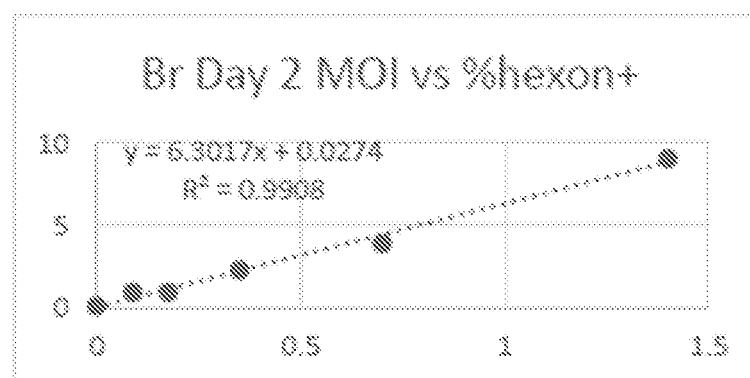
Figure 2C:
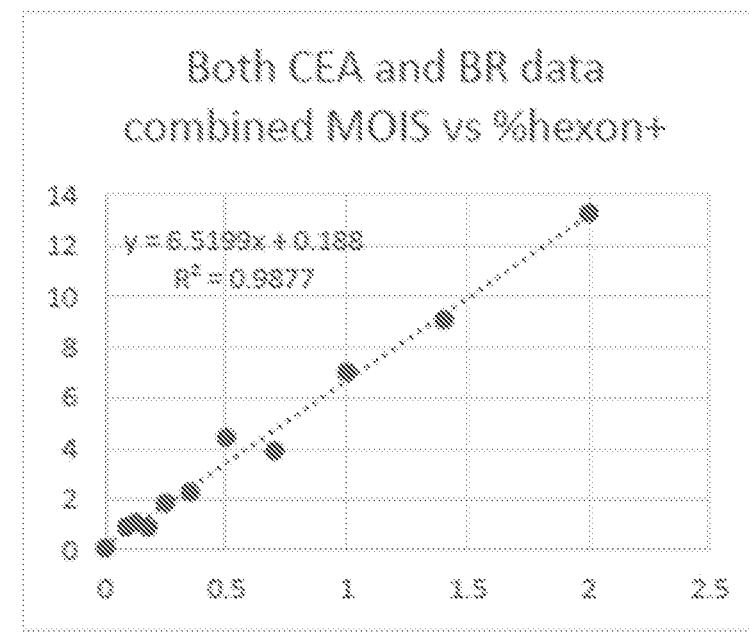

Cells are gated for hexon-positive live cells and quantification was carried out by analyzing the percentage of cells that were hexon-positive. FIGS. 2A-2C shows results from flow cytometry-based detection of hexon protein in E.C7 infected cells. FIG. 2A illustrates flow cytometry quantification of hexon protein expression in E.C7 cells infected with Ad-CEA. The x-axis indicates the multiplicity of infection (MOI) and the y-axis indicates the percentage of hexon positive cells. MOI is determined by infectious units (IFU) of Ad-CEA used in the infection of E.C7 cells divided by the number of E.C7 cells and, thus, captures the different concentrations of Ad-CEA virions incubated with E.C7 cells. FIG. 2B rates flow cytometry quantification of hexon protein expression in E.C7 cells infected with Ad-Brachyury. The x-axis indicates the multiplicity of infection (MOI) and the y-axis indicates the percentage of hexon positive cells. MOI is determined by infectious units (IFU) of Ad-CEA used in the infection of E.C7 cells divided by the number of E.C7 cells and, thus, captures the different concentrations of Ad-CEA virions incubated with E.C7 cells. FIG. 2C illustrates an overlay of FIG. 2A and FIG. 2B. These results demonstrate that the antibody-based flow cytometry assay can be used to generate a calibration curve, which can be used to quantify the IFUs/mL of adenovirus virions with cheaper reagent costs than the hexon assay.

Example 2

Figure 3A:
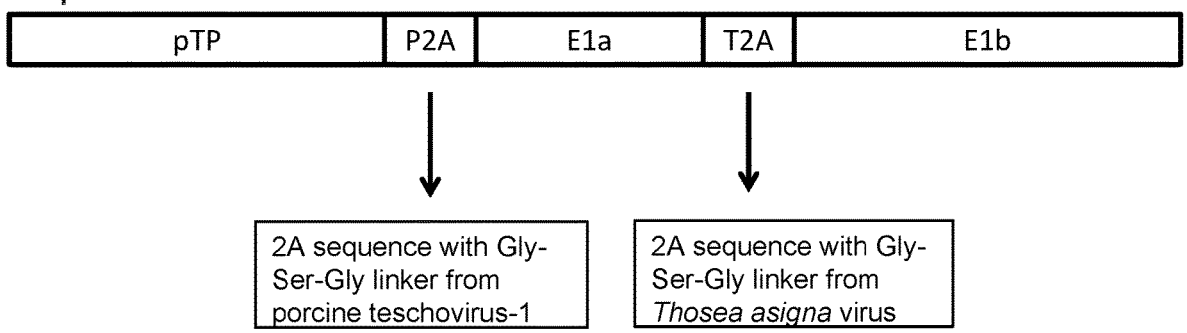
FIGS. 3A and 3B illustrate plasmid for transfecting suspension cells.
Figure 3B:
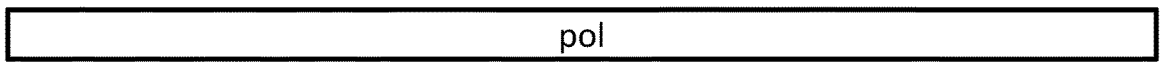

Antibody-Mediated Flow Cytometry Detection of Hexon Expression in Suspension Cells This example describes antibody-mediated flow cytometry detection of hexon expression in suspension cells to verify production of infectious adenovirus virions and to quantify infectious units (IFUs)/mL. Suspension cells are transfected with plasmids expressing adenovirus 5 pol, pTP, E1a, and E1b, allowing for replication of Ad5 [E1-, E2b-]. FIG. 3A illustrates the pTP, E1a, and E1b expression plasmid used to transfect suspension cells. This plasmid is a triple expression plasmid and is subcloned into BamHI>EcoRV site of pcDNA3.1(+), which is a mammalian expression vector resistant to neomycin/G418, and geneticin. The triple gene insert of FIG. 3A is ~3.5 kb (3540 base pairs). FIG. 3B illustrates the Pol expression plasmid used to transfect suspension cells. The plasmid is subcloned into BamHI>EcoRV sites of pcDNA3.1(+)hygro, which is a mammalian expression vector resistant to hygromycin. The gene insert of FIG. 3B is ~3.6 kb (3597 base pairs).

Suspension cells are transferred to 96-well plates and infected with a dilution series of adenovirus-containing media. Suspension cells are cultured with adenovirus-containing media for 48 hours after which cells were centrifuged. The cell pellet is resuspended and stained for live cells, fixed, permeabilized, and stained for hexon with a fluorophore-conjugated monoclonal antibody against hexon protein. Suspension cells are analyzed for fluorescence corresponding to hexon protein via flow cytometry. Suspension cells are gated for hexon-positive live cells and quantification is carried out by analyzing the percentage of cells that are hexon-positive. Suspension cells used in this assay are bone marrow-derived cells (e.g., K-562 cells), T-lymphoblast-derived cells (e.g., MOLT-4 cells), or T cell lymphoma (e.g., Jurkat E6-1 cells).

Example 3

Hexon Quantitation via Bio-Layer Interferometry (BLI)

This example describes hexon quantitation and correlation with infectivity via bio-layer interferometry (BLI). BLI is carried out using the BLITZ® System or an OCTETO® System (a BLI system that has eight arms and can, thus, process eight samples simultaneously) from Pall ForteBio. The glass biosensors are pre-coated with a protein that binds to the Fc domain of mouse antibodies or is pre-coated with streptavidin, which can capture biotinylated anti-hexon antibodies. Lysates are prepared from E.C7 cells producing the Ad5 [E1-, E2b-] vectors of the present disclosure and a dilution series of this lysate is passed over the glass biosensor and the biosensor is loaded in the BLITZ® or OCTET® systems. Mass accumulation on the tip of the optical biosensor is measured by the system, correlating to build up of hexon positive cells. Hexon-positive cells are quantitated in 5-30 minutes.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of quantifying the infectivity of adenoviral vector, the method comprising: transfecting a plasmid into adenoviral production cells, wherein the plasmid comprises (1) a polynucleotide encoding adenoviral proteins and (2) a polynucleotide insert encoding at least one tumor antigen;
propagating adenoviral vectors in the production cells;
purifying the adenoviral vectors by lysing the production cells and passing the lysate through an ion-exchange membrane to form a purified lysate;
loading the purified lysate onto an optical biosensor comprising a glass surface and an anti-hexon monoclonal antibody;
measuring biomass accumulation on the glass surface by bio-layer interferometry (BLI), wherein the accumulation correlates to a buildup of plasmid-transfected hexon positive production cells; and,
quantifying hexon positive production cells, wherein quantification of the purified lysate by BLI occurs within 5-30 minutes, and is correlated with infectivity of the adenoviral vector.

2. The method of claim 1, wherein the adenoviral vectors are propagated in the production cells for 40-96 hours.

3. The method of claim 1, wherein the adenoviral vectors are propagated in the production cells for 10 days.

4. The method of claim 1, wherein the quantification determines the infectivity of the adenoviral vector.

5. The method of claim 1, wherein the quantification yields an infectivity value in infectious units (IFU)/ml.

6. The method of claim 1, further comprising incubating quantified adenoviral vectors with a suspension cell line.

7. The method of claim 6, wherein the suspension cell is an E.C7 cell grown in a serum-free media.

8. The method of claim 6, wherein the suspension cell is a bone marrow-derived cell, a T-lymphoblast-derived cell, or a T cell lymphoma.

9. The method of claim 8, wherein the bone marrow-derived cell is a K-562 cell.

10. The method of claim 8, wherein the T-lymphoblast cell is a MOLT-4 cell.

11. The method of claim 8, wherein the T cell lymphoma is a Jurkat E6-1.

12. The method of claim 8, wherein the bone marrow-derived cell, the T- lymphoblast-derived cell, or the T cell lymphoma is transfected with adenovirus 5 pol, pTP, E1a, and E1b.

* * * * *

UNITED STATES PATENT AND TRADEMARK OFFICE
CERTIFICATE OF CORRECTION

| | |
|---|---|
| PATENT NO. | : 11,573,230 B2 |
| APPLICATION NO. | : 16/964325 |
| DATED | : February 7, 2023 |
| INVENTOR(S) | : Adrian E. Rice, Kayvan Niazi and Frank R. Jones |

It is certified that error appears in the above-identified patent and that said Letters Patent is hereby corrected as shown below:

In the Claims

In Column 33, Line 18, please delete "A method of quantifying the infectivity of adenoviral" and insert -- A method of quantifying the infectivity of an adenoviral --

In Column 34, Line 35, please delete "is a Jurkat E6-1." and insert -- is a Jurkat E6-1 cell. --

Signed and Sealed this
Eleventh Day of July, 2023

Katherine Kelly Vidal
*Director of the United States Patent and Trademark Office*

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 1

Thr Cys Thr Cys Thr Cys Cys Asn Ala
1               5